US008759645B2

(12) United States Patent
Frohberg et al.

(10) Patent No.: US 8,759,645 B2
(45) Date of Patent: Jun. 24, 2014

(54) WHEAT STARCH AND WHEAT FLOURS AND FOODSTUFFS CONTAINING THESE WHEAT STARCH/WHEAT FLOURS

(75) Inventors: Claus Frohberg, Kleinmachnow (DE); Ralf-Christian Schmidt, Stahnsdorf (DE)

(73) Assignee: Bayer Cropscience AG, Monheim (DE)

( * ) Notice: Subject to any disclaimer, the term of this patent is extended or adjusted under 35 U.S.C. 154(b) by 361 days.

(21) Appl. No.: 13/003,495

(22) PCT Filed: Jul. 9, 2009

(86) PCT No.: PCT/EP2009/005098

§ 371 (c)(1), (2), (4) Date: Jan. 10, 2011

(87) PCT Pub. No.: WO2010/003701

PCT Pub. Date: Jan. 14, 2010

(65) Prior Publication Data

US 2011/0296560 A1 Dec. 1, 2011

Related U.S. Application Data

(60) Provisional application No. 61/134,465, filed on Jul. 10, 2008.

(30) Foreign Application Priority Data

Jul. 10, 2008 (EP) .................................... 08075631

(51) Int. Cl.
*A23L 1/308* (2006.01)
*A01H 5/00* (2006.01)
*C12N 15/82* (2006.01)

(52) U.S. Cl.
USPC ....................................... 800/320.3; 435/468

(58) Field of Classification Search
None
See application file for complete search history.

(56) References Cited

U.S. PATENT DOCUMENTS 5,051,271 A 9/1991 Iyengar et al.
6,307,125 B1 * 10/2001 Block et al. .................. 800/284

FOREIGN PATENT DOCUMENTS

| | | | |
|---|---|---|---|
| EP | 564893 | A1 | 10/1993 |
| EP | 688872 | A1 | 12/1995 |
| EP | 0846704 | A2 | 6/1998 |
| EP | 0846704 | A3 | 6/1998 |
| WO | WO 2006/069442 | | 7/2006 |
| WO | WO 2007/009823 | | 1/2007 |
| WO | WO 2008/080630 | | 7/2008 |

OTHER PUBLICATIONS

Nakamura et al, 2005, Plant Mol, Bio., 58:213-227.*
Hung et al, 2005, Cereal Chemistry, 82:690-694.*
Jiang et al, 2005, Planta, 218:1062-1070.*
Nakamura et al, 2005, Plant Mol. Biol. 58:213-227.*
Chanvrier et al., Journal of Agricultural and Food Chemistry, vol. 55, pp. 10248-10257 (2007).
Eckhoff et al., Cereal Chemistry, vol. 73, pp. 54-57 (1996).
Englyst et al., British Journal of Nutrition, vol. 75, pp. 327-337 (1996).
Englyst et al., European Journal of Clinical Nutrition, vol. 46 (Suppl. 2), pp. S33-S50 (1992).
Evans et al., Cereal Chemistry, vol. 81, No. 1, pp. 31-37 (2004).
Faisant et al., Sciences des Aliments, vol. 15, pp. 83-89 (1995).
FAO Food and Nutrition Paper 66, "Carbohydrates in human nutrition", Chapter 4—The Role of the Glycemic Index in Food Choice, pp. 25-30, Report from Apr. 14-18, (1997).
Gao et al., Genome 43, vol. 5 pp. 768-775 (2000).
Hanashiro et al., Journal of Applied Glycoscience, vol. 51, pp. 217-221 (2004).
Hung et al., Cereal Chemistry vol. 82, pp. 690-694 (2005).
Hung et al., Trends in Food Science & Technology, vol. 17, pp. 448-456 (2006).
Jiang et al., Planta, vol. 218, pp. 1062-1070 (2004).
Knight et al., Starch, Chemistry and Technology, 2nd Edition, ISBN 0-12-746270-8, pp. 491-506 (1984).
Konik-Rose et al., Theoretical and Applied Genetics, vol. 115, pp. 1053-1065, (2007).
Luo et al., Starch/Starke, vol. 58, pp. 468-474 (2006).
McCleary et al., Journal of AOAC International, vol. 85, pp. 665-675 (2002).
Mikulikova et al., Czech Journal of Genetics and Plant Breeding, vol. 42, No. 3, pp. 95-102 (2006).
Morell et al., Journal of AOAC International, vol. 87, No. 3, pp. 740-748 (2004).
Morita et al., Cereal Chemistry, vol. 79, pp. 491-495 (2002).
Ral et al., Journal of Agricultural and Food Chemistry, pp. A-J (2008).
Regina et al., PNAS vol. 103, No. 10, pp. 3546-3551 (2006).
Senti et al., Tappi, vol. 43, No. 4, pp. 343-349 (1960).
Sestili et al., Proceedings of the 51st Italian Society of Agricultural Genetics Annual Congress (2007).
Shin et al., Cereal Chemistry, vol. 80, No. 5, pp. 564-566 (2003).
Shin et al., Starch/Starke, vol. 56, pp. 478-483 (2004).

(Continued)

*Primary Examiner* — Ashwin Mehta
*Assistant Examiner* — Jason Deveau Rosen
(74) *Attorney, Agent, or Firm* — Hunton & Williams LLP

(57) ABSTRACT

The present invention relates to wheat flours, the starch component whereof has an amylose content between 15.0 wt. % and 30.0 wt. % and which have a content of resistant starch of more than 5.0 wt. % and foodstuffs containing these wheat flours. Further, the present invention relates to methods for the production of said wheat flours and the use thereof as resistant starch, as a prebiotic or for the production of foodstuffs with decreased glycemic index. The present invention also relates to nucleic acid molecules which code for a soluble starch synthase II, and vectors containing such nucleic acid molecules. Further, the present invention also relates to host cells and plants which contain such nucleic acid molecules or vectors.

15 Claims, 2 Drawing Sheets

(56) References Cited

OTHER PUBLICATIONS

Skrabanja et al., Journal of Agricultural and Food Chemistry, vol. 49, pp. 490-496 (2001).
Wasserman et al, Journal of Thermal Analysis and Calorimetry, vol. 87, No. 1, pp. 153-157 (2007).
Wolever et al., American Journal of Clinical Nutrition, vol. 54, pp. 846-854 (1991).
Woo et al., Cereal Chemistry, vol. 79, No. 6, pp. 819-825 (2002).
Yahl et al., Microscope, vol. 32, pp. 123-132 (1984).
Yamamori et al., Australian Journal of Agricultural Research, vol. 57, pp. 531-535 (2006).
Yasui et al., Journal of Cereal Science, vol. 24, pp. 131-137 (1996).
European Search Report for European Application No. 08075631.5, mailed Dec. 15, 2008.
International Search Report for International Application No. PCT/EP2009/005098, mailed Oct. 12, 2009.
International Preliminary Report on Patentability for International Application No. PCT/EP2009/005098, mailed Jan. 20, 2011.

* cited by examiner

SEQUENCE LISTING

<160> NUMBER OF SEQ ID NOS: 18

<210> SEQ ID NO 1
<211> LENGTH: 2433
<212> TYPE: DNA
<213> ORGANISM: Oryza sativa

<400> SEQUENCE: 1
atgtcgtcgg ccgtcgtcgc gtcatccacc acgttcctcg tcgcgctcgc ctcttcggcg 60
tcacggggag ggcccaggag ggggagggtg gtgggcgtgg ccgcgccgcc ggccctgctt 120
tacgacggcc gcgccggaag gctagcccta cgggcgccgc ctccgccccg gcctcggcct 180
cggcgtcggg atgcgggcgt ggtgcgccgc gcggatgatg gggagaacga ggcggcggtg 240
gagcgggcgg gtgaggacga cgacgaggag gaggagttct cttcgggcgc gtggcagccg 300
ccccgctcgc gtcgcggcgg cgtcggcaag gtcttgaagc ggaggggcac cgtcccgccc 360
gtcggccggt acggctccgg cggtgatgcg gcgagagtgc gcggggcggc cgcgccggcg 420
ccggcgccga cacaggacgc cgcctcaagt aagaacggag cgcttctcag cggccgcgac 480
gacgacacac ctgcctcacg gaacggatcg gtcgttaccg gcgccgacaa gcctgccgcc 540
gccacgccgc cggtgaccat aacgaagctc ccagcgccgg actccccgt gatccttcca 600 tccgtagaca agccgcagcc ggagttcgtc atcccagacg cgacggcgcc ggcgccgcca 660
ccgcccggtt caaatcccag gtcgtccgct cctctcccca agcctgacaa ttcggaattt 720
gcagaggata agagcgcaaa agttgttgag agtgctccga agccaaaggc gactagatct 780
tcccctattc ctgcggtaga agaggagacg tgggatttca agaaatattt tgatctgaac 840
gaaccggacg ccgcggagga tggcgatgac gatgatgact gggctgattc agatgcgtca 900
gattctgaga tcgaccagga tgacgattcg ggccctttgg ctggggagaa tgtcatgaac 960
gtgatcgtgg tggctgctga atgttctccc tggtgcaaaa caggtgggct tggagatgtt 1020
gcaggtgctt tacccaaagc tttggcgagg agaggacatc gtgttatggt tgtggtacca 1080
aggtacggtg attacgcgga agcccaggat gtaggaatca ggaaatacta caaggctgct 1140
ggacaggatc tggaagtgaa atatttccat gcatttatcg atggagttga ttttgtgttc 1200
attgacgctc ctctcttccg tcaccgtcag gatgacatct atggggggaa cagacaggaa 1260

```
atcatgaagc gcatgattct gttttgtaag gctgctgttg aggttccttg gcacgttcca   1320

tgcggtggtg tgccctatgg ggatggcaac ttggtgttcc ttgcaaacga ttggcacact   1380

gcactcctgc ctgtttatct gaaggcatat tacagagaca atggcatgat gcagtacact   1440

cgctctgtcc ttgtgataca taatatcgct taccagggcc gtggcccagt agatgaattc   1500

ccctacatgg aattgccgga gcactacctg gatcacttca agctgtacga ccccgtcggc   1560

ggcgagcacg ccaacatctt cggcgcgggc ctgaagatgg cggaccgggt ggtgaccgtg   1620

agccccggct acctctggga gctgaagacg acggagggcg gctggggcct ccacgacatc   1680

atacgggaga acgactggaa gatgaacggc atcgtgaacg gcatcgacta ccgggagtgg   1740

aacccggagg tggacgtgca cctgcagtcc gacggctacg ccaactacac cgtggcctcg   1800

ctggactcca gcaagccgcg gtgcaaggcg gcgctgcagc gcgagctggg gctggaggtg   1860

cgcgacgacg tgccgctgat cgggttcatc gggcggctcg acgggcagaa aggtgtggac   1920

atcatcggcg acgcgatgcc gtggatcgcc gggcaggacg tgcagctggt gctgctgggc   1980

tccggccgcc gcgacctgga ggtgatgctg cagcggttcg aggcgcagca caacagcaag   2040

gtgcgcgggt gggtggggtt ctcggtgaag atggcgcacc ggatcacggc gggcgccgac   2100

gtgctggtca tgccgtcgcg gttcgagccg tgcggcctca accagctcta cgccatggcg   2160

tacggcaccg tccccgtcgt gcacgccgtc ggcgggctga gggacaccat gtcggcgttc   2220

gacccgttcg aggacaccgg cctcgggtgg acgttcgacc gcgccgagcc gcacaagctc   2280

atcgaggcgc tcggccactg cctcgagacg taccgcaagt acaaggagag ctggaggggg   2340

ctccaggtgc gcggcatgtc gcaggacctc agctgggacc acgccgccga gctctacgag   2400

gaggtccttg tcaaggccaa gtaccaatgg tga                                2433
```

```
<210> SEQ ID NO 2
<211> LENGTH: 810
<212> TYPE: PRT
<213> ORGANISM: Oryza sativa

<400> SEQUENCE: 2

Met Ser Ser Ala Val Val Ala Ser Ser Thr Thr Phe Leu Val Ala Leu
1               5                   10                  15

Ala Ser Ser Ala Ser Arg Gly Gly Pro Arg Arg Gly Arg Val Val Gly
            20                  25                  30

Val Ala Ala Pro Pro Ala Leu Leu Tyr Asp Gly Arg Ala Gly Arg Leu
        35                  40                  45

Ala Leu Arg Ala Pro Pro Pro Pro Arg Pro Arg Pro Arg Arg Arg Asp
    50                  55                  60

Ala Gly Val Val Arg Arg Ala Asp Asp Gly Glu Asn Glu Ala Ala Val
65                  70                  75                  80

Glu Arg Ala Gly Glu Asp Asp Asp Glu Glu Glu Glu Phe Ser Ser Gly
                85                  90                  95

Ala Trp Gln Pro Pro Arg Ser Arg Arg Gly Gly Val Gly Lys Val Leu
            100                 105                 110

Lys Arg Arg Gly Thr Val Pro Pro Val Gly Arg Tyr Gly Ser Gly Gly
        115                 120                 125

Asp Ala Ala Arg Val Arg Gly Ala Ala Ala Pro Ala Pro Ala Pro Thr
    130                 135                 140

Gln Asp Ala Ala Ser Ser Lys Asn Gly Ala Leu Leu Ser Gly Arg Asp
145                 150                 155                 160
```

```
Asp Asp Thr Pro Ala Ser Arg Asn Gly Ser Val Val Thr Gly Ala Asp
                165                 170                 175

Lys Pro Ala Ala Ala Thr Pro Pro Val Thr Ile Thr Lys Leu Pro Ala
            180                 185                 190

Pro Asp Ser Pro Val Ile Leu Pro Ser Val Asp Lys Pro Gln Pro Glu
        195                 200                 205

Phe Val Ile Pro Asp Ala Thr Ala Pro Ala Pro Pro Pro Pro Gly Ser
    210                 215                 220

Asn Pro Arg Ser Ser Ala Pro Leu Pro Lys Pro Asp Asn Ser Glu Phe
225                 230                 235                 240

Ala Glu Asp Lys Ser Ala Lys Val Val Glu Ser Ala Pro Lys Pro Lys
                245                 250                 255

Ala Thr Arg Ser Ser Pro Ile Pro Ala Val Glu Glu Glu Thr Trp Asp
            260                 265                 270

Phe Lys Lys Tyr Phe Asp Leu Asn Glu Pro Asp Ala Ala Glu Asp Gly
        275                 280                 285

Asp Asp Asp Asp Asp Trp Ala Asp Ser Asp Ala Ser Asp Ser Glu Ile
    290                 295                 300

Asp Gln Asp Asp Asp Ser Gly Pro Leu Ala Gly Glu Asn Val Met Asn
305                 310                 315                 320

Val Ile Val Val Ala Ala Glu Cys Ser Pro Trp Cys Lys Thr Gly Gly
                325                 330                 335

Leu Gly Asp Val Ala Gly Ala Leu Pro Lys Ala Leu Ala Arg Arg Gly
            340                 345                 350

His Arg Val Met Val Val Val Pro Arg Tyr Gly Asp Tyr Ala Glu Ala
        355                 360                 365

Gln Asp Val Gly Ile Arg Lys Tyr Tyr Lys Ala Ala Gly Gln Asp Leu
    370                 375                 380

Glu Val Lys Tyr Phe His Ala Phe Ile Asp Gly Val Asp Phe Val Phe
385                 390                 395                 400

Ile Asp Ala Pro Leu Phe Arg His Arg Gln Asp Asp Ile Tyr Gly Gly
                405                 410                 415

Asn Arg Gln Glu Ile Met Lys Arg Met Ile Leu Phe Cys Lys Ala Ala
            420                 425                 430

Val Glu Val Pro Trp His Val Pro Cys Gly Gly Val Pro Tyr Gly Asp
        435                 440                 445

Gly Asn Leu Val Phe Leu Ala Asn Asp Trp His Thr Ala Leu Leu Pro
    450                 455                 460

Val Tyr Leu Lys Ala Tyr Tyr Arg Asp Asn Gly Met Met Gln Tyr Thr
465                 470                 475                 480

Arg Ser Val Leu Val Ile His Asn Ile Ala Tyr Gln Gly Arg Gly Pro
                485                 490                 495

Val Asp Glu Phe Pro Tyr Met Glu Leu Pro Glu His Tyr Leu Asp His
            500                 505                 510

Phe Lys Leu Tyr Asp Pro Val Gly Gly Glu His Ala Asn Ile Phe Gly
        515                 520                 525

Ala Gly Leu Lys Met Ala Asp Arg Val Val Thr Val Ser Pro Gly Tyr
    530                 535                 540

Leu Trp Glu Leu Lys Thr Thr Glu Gly Gly Trp Gly Leu His Asp Ile
545                 550                 555                 560

Ile Arg Glu Asn Asp Trp Lys Met Asn Gly Ile Val Asn Gly Ile Asp
                565                 570                 575

Tyr Arg Glu Trp Asn Pro Glu Val Asp Val His Leu Gln Ser Asp Gly
```

```
            580                 585                 590

Tyr Ala Asn Tyr Thr Val Ala Ser Leu Asp Ser Ser Lys Pro Arg Cys
        595                 600                 605

Lys Ala Ala Leu Gln Arg Glu Leu Gly Leu Glu Val Arg Asp Asp Val
    610                 615                 620

Pro Leu Ile Gly Phe Ile Gly Arg Leu Asp Gly Gln Lys Gly Val Asp
625                 630                 635                 640

Ile Ile Gly Asp Ala Met Pro Trp Ile Ala Gly Gln Asp Val Gln Leu
                645                 650                 655

Val Leu Leu Gly Ser Gly Arg Arg Asp Leu Glu Val Met Leu Gln Arg
            660                 665                 670

Phe Glu Ala Gln His Asn Ser Lys Val Arg Gly Trp Val Gly Phe Ser
        675                 680                 685

Val Lys Met Ala His Arg Ile Thr Ala Gly Ala Asp Val Leu Val Met
    690                 695                 700

Pro Ser Arg Phe Glu Pro Cys Gly Leu Asn Gln Leu Tyr Ala Met Ala
705                 710                 715                 720

Tyr Gly Thr Val Pro Val Val His Ala Val Gly Gly Leu Arg Asp Thr
                725                 730                 735

Met Ser Ala Phe Asp Pro Phe Glu Asp Thr Gly Leu Gly Trp Thr Phe
            740                 745                 750

Asp Arg Ala Glu Pro His Lys Leu Ile Glu Ala Leu Gly His Cys Leu
        755                 760                 765

Glu Thr Tyr Arg Lys Tyr Lys Glu Ser Trp Arg Gly Leu Gln Val Arg
    770                 775                 780

Gly Met Ser Gln Asp Leu Ser Trp Asp His Ala Ala Glu Leu Tyr Glu
785                 790                 795                 800

Glu Val Leu Val Lys Ala Lys Tyr Gln Trp
                805                 810


<210> SEQ ID NO 3
<211> LENGTH: 2433
<212> TYPE: DNA
<213> ORGANISM: Artificial Sequence
<220> FEATURE:
<223> OTHER INFORMATION: Synthetic DNA, mutation at position 2209

<400> SEQUENCE: 3

atgtctagcg cggtggttgc gtccagcaca acttttctcg tcgcacttgc ctctagcgcg      60

agccggggcg ggccacgtag ggggcgcgtc gtgggcgtgg ccgctccccc agccctcctg     120

tatgacggga gagctggcag gctagccctg cgcgcccctc cgccaccccg ccctagacct     180

aggcgcaggg atgcgggtgt tgtcaggcgg gctgatgacg gggagaacga ggccgcagtg     240

gagcgggccg gcgaggacga tgacgaggag gaggagttct cgtccggggc ctggcagcca     300

ccgcgttcaa ggcgcggtgg agttggcaag gtcctcaaac gtcgcggtac cgtgccgcca     360

gtcggaaggt acggctccgg tggagacgcc gctcgggtga gaggagccgc ggcacccgct     420

ccagcaccga cgcaagacgc agcgtcgtct aagaatggcg cgcttttgtc aggcagggat     480

gacgacacac ctgcctcacg gaacggatcg gtcgttaccg gcgccgacaa gcctgccgcc     540

gccacgccgc cggtgaccat aacgaagctc ccagcgccgg actcccccgt gatccttcca     600

tccgtagaca agccgcagcc ggagttcgtc atcccagacg cgacggcgcc ggcgccgcca     660

ccgcccggtt caaatcccag gtcgtccgct cctctcccca agcctgacaa ttcggaattt     720

gcagaggata agagcgcaaa agttgttgag agtgctccga agccaaaggc gactagatct     780
```

```
tcccctattc ctgcggtaga agaggagacg tgggatttca agaaatattt tgatctgaac    840
gaaccggacg ccgcggagga tggcgatgac gatgatgact gggctgattc agatgcgtca    900
gattctgaga tcgaccagga tgacgattcg ggtcctttgg ctggggagaa tgtcatgaac    960
gtgatcgtgg tggctgctga atgttctccc tggtgcaaaa caggtgggct tggagatgtt   1020
gcaggtgctt tacccaaggc tttggcgagg agaggacatc gtgttatggt tgtcgtacca   1080
aggtacggtg attacgcgga agcccaggat gtaggaatca ggaaatacta caaggctgct   1140
ggacaggatc tggaagtgaa atatttccat gcatttatcg acggagttga ttttgtgttc   1200
attgacgctc ctctcttccg tcaccgtcag gatgacatct atgggggcaa cagacaggaa   1260
atcatgaagc gcatgattct gttttgtaag gctgctgttg aggttccttg gcacgttcca   1320
tgcggtggtg tgccctatgg ggatggcaac ttggtgttcc ttgcaaacga ttggcacact   1380
gcactcctgc ctgtttatct gaaggcatat tacagagaca atggcatgat gcagtacact   1440
cgctctgtcc ttgtgataca taatatcgct taccagggcc gtggcccagt agatgaattc   1500
ccctacatgg aattgccgga gcactacctg gatcacttca agctgtacga ccccgtcggc   1560
ggcgagcacg ccaacatctt cggcgcgggc ctgaagatgg cggaccgggt ggtgaccgtg   1620
agccccggct acctctggga gctgaagacg acggagggcg gctggggcct ccacgacatc   1680
atacgggaga acgactggaa gatgaacggc atcgtgaacg gcatcgacta ccgggagtgg   1740
aacccggagg tggacgtgca cctgcagtcc gacggctacg ccaactacac cgtggcctcg   1800
ctggactcca gcaagccgcg gtgcaaggcg gcgctgcagc gcgagctggg gctggaggtg   1860
cgcgacgacg tgccgctgat cggtttcatc gggcggctcg acgggcagaa aggtgtggac   1920
atcatcggcg acgcgatgcc gtggatcgcc gggcaggacg tgcagctggt gctgctgggc   1980
tccggccgcc gcgacctgga ggtgatgctg cagcggttcg aggcgcagca caacagcaag   2040
gtgcgcgggt gggtggggtt ctcggtgaag atggcgcacc ggatcacggc gggcgccgac   2100
gtgctggtca tgccgtcgcg gttcgagccg tgcggcctca accagctcta cgccatggcg   2160
tacggcaccg tccccgtcgt gcacgccgtc ggcgggctga gggacaccgt gtcggcgttc   2220
gacccgttcg aggacaccgg cctcgggtgg acgttcgacc gcgccgagcc gcacaagctc   2280
atcgaggcgc tcggccactg cctggagacg taccgcaagt acaaggagag ctggaggggg   2340
ctccaggtgc gcggcatgtc gcaggacctc agctgggacc acgccgccga gctctacgag   2400
gaggtccttg tcaaggccaa gtaccaatgg tga                                2433
```

<210> SEQ ID NO 4
<211> LENGTH: 810
<212> TYPE: PRT
<213> ORGANISM: Artificial Sequence
<220> FEATURE:
<223> OTHER INFORMATION: Point mutation of amino acid 737 (valin instead of methionin)

<400> SEQUENCE: 4

```
Met Ser Ser Ala Val Val Ala Ser Ser Thr Thr Phe Leu Val Ala Leu
1               5                   10                  15

Ala Ser Ser Ala Ser Arg Gly Gly Pro Arg Arg Gly Arg Val Val Gly
            20                  25                  30

Val Ala Ala Pro Pro Ala Leu Leu Tyr Asp Gly Arg Ala Gly Arg Leu
        35                  40                  45

Ala Leu Arg Ala Pro Pro Pro Pro Arg Pro Arg Pro Arg Arg Arg Asp
    50                  55                  60
```

```
Ala Gly Val Val Arg Arg Ala Asp Asp Gly Glu Asn Glu Ala Ala Val
65                  70                  75                  80

Glu Arg Ala Gly Glu Asp Asp Asp Glu Glu Glu Glu Phe Ser Ser Gly
                85                  90                  95

Ala Trp Gln Pro Pro Arg Ser Arg Arg Gly Gly Val Gly Lys Val Leu
            100                 105                 110

Lys Arg Arg Gly Thr Val Pro Pro Val Gly Arg Tyr Gly Ser Gly Gly
        115                 120                 125

Asp Ala Ala Arg Val Arg Gly Ala Ala Ala Pro Ala Pro Ala Pro Thr
    130                 135                 140

Gln Asp Ala Ala Ser Ser Lys Asn Gly Ala Leu Leu Ser Gly Arg Asp
145                 150                 155                 160

Asp Asp Thr Pro Ala Ser Arg Asn Gly Ser Val Val Thr Gly Ala Asp
                165                 170                 175

Lys Pro Ala Ala Ala Thr Pro Pro Val Thr Ile Thr Lys Leu Pro Ala
            180                 185                 190

Pro Asp Ser Pro Val Ile Leu Pro Ser Val Asp Lys Pro Gln Pro Glu
        195                 200                 205

Phe Val Ile Pro Asp Ala Thr Ala Pro Ala Pro Pro Pro Pro Gly Ser
    210                 215                 220

Asn Pro Arg Ser Ser Ala Pro Leu Pro Lys Pro Asp Asn Ser Glu Phe
225                 230                 235                 240

Ala Glu Asp Lys Ser Ala Lys Val Val Glu Ser Ala Pro Lys Pro Lys
                245                 250                 255

Ala Thr Arg Ser Ser Pro Ile Pro Ala Val Glu Glu Glu Thr Trp Asp
            260                 265                 270

Phe Lys Lys Tyr Phe Asp Leu Asn Glu Pro Asp Ala Ala Glu Asp Gly
        275                 280                 285

Asp Asp Asp Asp Asp Trp Ala Asp Ser Asp Ala Ser Asp Ser Glu Ile
    290                 295                 300

Asp Gln Asp Asp Asp Ser Gly Pro Leu Ala Gly Glu Asn Val Met Asn
305                 310                 315                 320

Val Ile Val Val Ala Ala Glu Cys Ser Pro Trp Cys Lys Thr Gly Gly
                325                 330                 335

Leu Gly Asp Val Ala Gly Ala Leu Pro Lys Ala Leu Ala Arg Arg Gly
            340                 345                 350

His Arg Val Met Val Val Val Pro Arg Tyr Gly Asp Tyr Ala Glu Ala
        355                 360                 365

Gln Asp Val Gly Ile Arg Lys Tyr Tyr Lys Ala Ala Gly Gln Asp Leu
    370                 375                 380

Glu Val Lys Tyr Phe His Ala Phe Ile Asp Gly Val Asp Phe Val Phe
385                 390                 395                 400

Ile Asp Ala Pro Leu Phe Arg His Arg Gln Asp Asp Ile Tyr Gly Gly
                405                 410                 415

Asn Arg Gln Glu Ile Met Lys Arg Met Ile Leu Phe Cys Lys Ala Ala
            420                 425                 430

Val Glu Val Pro Trp His Val Pro Cys Gly Gly Val Pro Tyr Gly Asp
        435                 440                 445

Gly Asn Leu Val Phe Leu Ala Asn Asp Trp His Thr Ala Leu Leu Pro
    450                 455                 460

Val Tyr Leu Lys Ala Tyr Tyr Arg Asp Asn Gly Met Met Gln Tyr Thr
465                 470                 475                 480
```

```
Arg Ser Val Leu Val Ile His Asn Ile Ala Tyr Gln Gly Arg Gly Pro
                485                 490                 495

Val Asp Glu Phe Pro Tyr Met Glu Leu Pro Glu His Tyr Leu Asp His
            500                 505                 510

Phe Lys Leu Tyr Asp Pro Val Gly Gly Glu His Ala Asn Ile Phe Gly
        515                 520                 525

Ala Gly Leu Lys Met Ala Asp Arg Val Val Thr Val Ser Pro Gly Tyr
    530                 535                 540

Leu Trp Glu Leu Lys Thr Thr Glu Gly Gly Trp Gly Leu His Asp Ile
545                 550                 555                 560

Ile Arg Glu Asn Asp Trp Lys Met Asn Gly Ile Val Asn Gly Ile Asp
                565                 570                 575

Tyr Arg Glu Trp Asn Pro Glu Val Asp Val His Leu Gln Ser Asp Gly
            580                 585                 590

Tyr Ala Asn Tyr Thr Val Ala Ser Leu Asp Ser Ser Lys Pro Arg Cys
        595                 600                 605

Lys Ala Ala Leu Gln Arg Glu Leu Gly Leu Glu Val Arg Asp Asp Val
    610                 615                 620

Pro Leu Ile Gly Phe Ile Gly Arg Leu Asp Gly Gln Lys Gly Val Asp
625                 630                 635                 640

Ile Ile Gly Asp Ala Met Pro Trp Ile Ala Gly Gln Asp Val Gln Leu
                645                 650                 655

Val Leu Leu Gly Ser Gly Arg Arg Asp Leu Glu Val Met Leu Gln Arg
            660                 665                 670

Phe Glu Ala Gln His Asn Ser Lys Val Arg Gly Trp Val Gly Phe Ser
        675                 680                 685

Val Lys Met Ala His Arg Ile Thr Ala Gly Ala Asp Val Leu Val Met
    690                 695                 700

Pro Ser Arg Phe Glu Pro Cys Gly Leu Asn Gln Leu Tyr Ala Met Ala
705                 710                 715                 720

Tyr Gly Thr Val Pro Val Val His Ala Val Gly Gly Leu Arg Asp Thr
                725                 730                 735

Val Ser Ala Phe Asp Pro Phe Glu Asp Thr Gly Leu Gly Trp Thr Phe
            740                 745                 750

Asp Arg Ala Glu Pro His Lys Leu Ile Glu Ala Leu Gly His Cys Leu
        755                 760                 765

Glu Thr Tyr Arg Lys Tyr Lys Glu Ser Trp Arg Gly Leu Gln Val Arg
    770                 775                 780

Gly Met Ser Gln Asp Leu Ser Trp Asp His Ala Ala Glu Leu Tyr Glu
785                 790                 795                 800

Glu Val Leu Val Lys Ala Lys Tyr Gln Trp
                805                 810
```

<210> SEQ ID NO 5
<211> LENGTH: 2400
<212> TYPE: DNA
<213> ORGANISM: Artificial Sequence
<220> FEATURE:
<223> OTHER INFORMATION: Synthetic sequence

<400> SEQUENCE: 5

```
atgtcgagcg cagtcgcttc tgcagcgagt ttcctggcgc tggcttcggc ctccccgggg     60

cgttcccgga ggcgggccag ggttagcgcc cagccgccac acgcaggcgc cggtaggctg    120

cattggccgc catggccgcc acaaagaact gcgcgcgacg gcgccgttgc agccctcgca    180
```

```
gctggaaaga aggacgctgg gatcgatgac gcggcagcca gtgtgaggca accgcgcgca    240
ttgcgggggg gagccgctac aaaggtggcg gagagacggg atccagtcaa gaccctggac    300
cgtgacgcgg ccgagggcgg gggcccatca cctccggccg cgcggcaaga cgcggcaagg    360
ccaccttcta tgaacgggat gcccgtcaac ggggagaata agtccacggg tggcgggggc    420
gcgacgaagg attctgggct accaacccct gcgcgtgccc cccatccgag tactcagaac    480
cgcgcccccg tgaatggtga gaacaaggcg aacgtcgcgt ccccaccgac ctctatcgca    540
gaagcggcag ccagcgattc agctgcgacg atctcaatta gcgacaaggc tccggagtct    600
gtggtccccg cagagaagac acctccatca tctggcagca acttcgagtc aagcgcatcg    660
gcgccaggct ccgacacggt gagcgacgtc gagcaggagc tcaagaaggg agccgtcgtg    720
gttgaggaag cccctaagcc gaaggctctc tccccacccg ctgcacctgc tgtgcaggaa    780
gatctgtggg acttcaagaa gtatatcggc tttgaggaac cagttgaagc caaggacgat    840
ggcagggctg tggcggacga tgccgggagc ttcgaacacc atcagaacca cgattccggg    900
ccactcgcgg gggagaacgt gatgaacgtg gttgtggttg ccgctgagtg ctcgccctgg    960
tgtaagacag gtggactggg cgatgtcgcg ggagcactcc caaaggccct tgctaagaga   1020
gggcatcgtg tgatggtcgt ggtccccagg tatggcgact acgaggaagc atatgacgtt   1080
ggcgtcagga agtactataa ggctgccggg caggacatgg aggtcaacta ctttcatgcc   1140
tacattgacg gagtggattt cgtctttatt gatgctccac tcttcaggca ccgccaggaa   1200
gatatttacg gtggctccag gcaagagatc atgaagagaa tgattctatt ttgcaaggcg   1260
gccgtcgagg tcccctggca cgtgccatgc gggggtgtgc catacggcga tggcaacttg   1320
gtctttatcg ccaatgactg gcacaccgct ctgctccctg tctatttgaa ggcctattac   1380
cgcgatcacg gactgatgca atacacccgt tccatcatgg tgatccataa tattgcacac   1440
cagggacgcg gccccgtgga tgagtttccg ttcacagagc ttcccgaaca ctacctggag   1500
cacttccggc tatacgatcc ggtgggcggt gagcacgcaa actacttcgc tgcgggtctc   1560
aagatggccg accaagttgt cgttgtgtcc ccagggtacc tctgggagtt gaagactgtg   1620
gaaggtggct ggggactgca cgacatcatt cgccaaaacg actggaagac gcgcggcatc   1680
gttaatggca ttgacaatat ggagtggaat ccagaggtcg acgcgcattt gaagagtgac   1740
gggtacacta acttctcact aaggacgctt gacagcggaa agcggcaatg taaggaggcc   1800
ctccaaaggg aactcggcct ccaagtgagg gccgacgtgc ctctcctggg cttcatcgga   1860
agactcgacg gccaaaaggg ggtggaaatc atcgccgatg ccatgccatg gatcgtctct   1920
caggacgtcc agcttgtgat gttgggtacc ggccgccatg acttggagtc gatgctccaa   1980
cattttgaga gggagcatca cgacaaggtt cggggatggg tgggattcag cgtgcgccta   2040
gctcatagga tcacagccgg cgccgacgcc ctccttatgc cctcgagatt cgaaccgtgc   2100
ggactcaatc agctctatgc catggcgtac gggaccgtcc ctgtggttca cgcggtggga   2160
ggtttgcgcg acaccgttcc tccctttgat ccatttaatc actccggtct gggctggacc   2220
ttcgatcgtg ccgaggccca caagctcatc gaggccctcg gtcactgcct gaggacttac   2280
cgcgacttta aggaaagctg gagagccctc caagagcgcg ggatgtccca ggatttctca   2340
tgggagcatg ccgcgaagct ttacgaggac gttctcgtga aggccaagta ccaatggtga   2400
```

<210> SEQ ID NO 6
<211> LENGTH: 799
<212> TYPE: PRT
<213> ORGANISM: Triticum aestivum

<400> SEQUENCE: 6

```
Met Ser Ser Ala Val Ala Ser Ala Ala Ser Phe Leu Ala Leu Ala Ser
1               5                   10                  15

Ala Ser Pro Gly Arg Ser Arg Arg Arg Ala Arg Val Ser Ala Gln Pro
            20                  25                  30

Pro His Ala Gly Ala Gly Arg Leu His Trp Pro Pro Trp Pro Pro Gln
        35                  40                  45

Arg Thr Ala Arg Asp Gly Ala Val Ala Ala Leu Ala Ala Gly Lys Lys
    50                  55                  60

Asp Ala Gly Ile Asp Asp Ala Ala Ala Ser Val Arg Gln Pro Arg Ala
65                  70                  75                  80

Leu Arg Gly Gly Ala Ala Thr Lys Val Ala Glu Arg Arg Asp Pro Val
                85                  90                  95

Lys Thr Leu Asp Arg Asp Ala Ala Glu Gly Gly Gly Pro Ser Pro Pro
            100                 105                 110

Ala Ala Arg Gln Asp Ala Ala Arg Pro Pro Ser Met Asn Gly Met Pro
        115                 120                 125

Val Asn Gly Glu Asn Lys Ser Thr Gly Gly Gly Gly Ala Thr Lys Asp
    130                 135                 140

Ser Gly Leu Pro Thr Pro Ala Arg Ala Pro His Pro Ser Thr Gln Asn
145                 150                 155                 160

Arg Ala Pro Val Asn Gly Glu Asn Lys Ala Asn Val Ala Ser Pro Pro
                165                 170                 175

Thr Ser Ile Ala Glu Ala Ala Ala Ser Asp Ser Ala Ala Thr Ile Ser
            180                 185                 190

Ile Ser Asp Lys Ala Pro Glu Ser Val Val Pro Ala Glu Lys Thr Pro
        195                 200                 205

Pro Ser Ser Gly Ser Asn Phe Glu Ser Ser Ala Ser Ala Pro Gly Ser
    210                 215                 220

Asp Thr Val Ser Asp Val Glu Gln Glu Leu Lys Lys Gly Ala Val Val
225                 230                 235                 240

Val Glu Glu Ala Pro Lys Pro Lys Ala Leu Ser Pro Pro Ala Ala Pro
                245                 250                 255

Ala Val Gln Glu Asp Leu Trp Asp Phe Lys Lys Tyr Ile Gly Phe Glu
            260                 265                 270

Glu Pro Val Glu Ala Lys Asp Asp Gly Arg Ala Val Ala Asp Asp Ala
        275                 280                 285

Gly Ser Phe Glu His His Gln Asn His Asp Ser Gly Pro Leu Ala Gly
    290                 295                 300

Glu Asn Val Met Asn Val Val Val Val Ala Ala Glu Cys Ser Pro Trp
305                 310                 315                 320

Cys Lys Thr Gly Gly Leu Gly Asp Val Ala Gly Ala Leu Pro Lys Ala
                325                 330                 335

Leu Ala Lys Arg Gly His Arg Val Met Val Val Val Pro Arg Tyr Gly
            340                 345                 350

Asp Tyr Glu Glu Ala Tyr Asp Val Gly Val Arg Lys Tyr Tyr Lys Ala
        355                 360                 365

Ala Gly Gln Asp Met Glu Val Asn Tyr Phe His Ala Tyr Ile Asp Gly
    370                 375                 380

Val Asp Phe Val Phe Ile Asp Ala Pro Leu Phe Arg His Arg Gln Glu
385                 390                 395                 400

Asp Ile Tyr Gly Gly Ser Arg Gln Glu Ile Met Lys Arg Met Ile Leu
```

```
                405                 410                 415

Phe Cys Lys Ala Ala Val Glu Val Pro Trp His Val Pro Cys Gly Gly
            420                 425                 430

Val Pro Tyr Gly Asp Gly Asn Leu Val Phe Ile Ala Asn Asp Trp His
        435                 440                 445

Thr Ala Leu Leu Pro Val Tyr Leu Lys Ala Tyr Tyr Arg Asp His Gly
    450                 455                 460

Leu Met Gln Tyr Thr Arg Ser Ile Met Val Ile His Asn Ile Ala His
465                 470                 475                 480

Gln Gly Arg Gly Pro Val Asp Glu Phe Pro Phe Thr Glu Leu Pro Glu
                485                 490                 495

His Tyr Leu Glu His Phe Arg Leu Tyr Asp Pro Val Gly Gly Glu His
            500                 505                 510

Ala Asn Tyr Phe Ala Ala Gly Leu Lys Met Ala Asp Gln Val Val Val
        515                 520                 525

Val Ser Pro Gly Tyr Leu Trp Glu Leu Lys Thr Val Glu Gly Gly Trp
    530                 535                 540

Gly Leu His Asp Ile Ile Arg Gln Asn Asp Trp Lys Thr Arg Gly Ile
545                 550                 555                 560

Val Asn Gly Ile Asp Asn Met Glu Trp Asn Pro Glu Val Asp Ala His
                565                 570                 575

Leu Lys Ser Asp Gly Tyr Thr Asn Phe Ser Leu Arg Thr Leu Asp Ser
            580                 585                 590

Gly Lys Arg Gln Cys Lys Glu Ala Leu Gln Arg Glu Leu Gly Leu Gln
        595                 600                 605

Val Arg Ala Asp Val Pro Leu Leu Gly Phe Ile Gly Arg Leu Asp Gly
    610                 615                 620

Gln Lys Gly Val Glu Ile Ile Ala Asp Ala Met Pro Trp Ile Val Ser
625                 630                 635                 640

Gln Asp Val Gln Leu Val Met Leu Gly Thr Gly Arg His Asp Leu Glu
                645                 650                 655

Ser Met Leu Gln His Phe Glu Arg Glu His His Asp Lys Val Arg Gly
            660                 665                 670

Trp Val Gly Phe Ser Val Arg Leu Ala His Arg Ile Thr Ala Gly Ala
        675                 680                 685

Asp Ala Leu Leu Met Pro Ser Arg Phe Glu Pro Cys Gly Leu Asn Gln
    690                 695                 700

Leu Tyr Ala Met Ala Tyr Gly Thr Val Pro Val Val His Ala Val Gly
705                 710                 715                 720

Gly Leu Arg Asp Thr Val Pro Pro Phe Asp Pro Phe Asn His Ser Gly
                725                 730                 735

Leu Gly Trp Thr Phe Asp Arg Ala Glu Ala His Lys Leu Ile Glu Ala
            740                 745                 750

Leu Gly His Cys Leu Arg Thr Tyr Arg Asp Phe Lys Glu Ser Trp Arg
        755                 760                 765

Ala Leu Gln Glu Arg Gly Met Ser Gln Asp Phe Ser Trp Glu His Ala
    770                 775                 780

Ala Lys Leu Tyr Glu Asp Val Leu Val Lys Ala Lys Tyr Gln Trp
785                 790                 795
```

<210> SEQ ID NO 7
<211> LENGTH: 13
<212> TYPE: PRT
<213> ORGANISM: Artificial Sequence
<220> FEATURE:
<223> OTHER INFORMATION: Peptide

<400> SEQUENCE: 7

Pro Val Val His Ala Val Gly Gly Leu Arg Asp Thr Val
1 5 10

<210> SEQ ID NO 8
<211> LENGTH: 5
<212> TYPE: PRT
<213> ORGANISM: Artificial Sequence
<220> FEATURE:
<223> OTHER INFORMATION: Peptide
<220> FEATURE:
<221> NAME/KEY: misc_feature
<222> LOCATION: (3)..(4)
<223> OTHER INFORMATION: Xaa can be any naturally occurring amino acid

<400> SEQUENCE: 8

Ser Trp Xaa Xaa Ile
1 5

<210> SEQ ID NO 9
<211> LENGTH: 5
<212> TYPE: PRT
<213> ORGANISM: Artificial Sequence
<220> FEATURE:
<223> OTHER INFORMATION: Peptide
<220> FEATURE:
<221> NAME/KEY: misc_feature
<222> LOCATION: (3)..(4)
<223> OTHER INFORMATION: Xaa can be any naturally occurring amino acid

<400> SEQUENCE: 9

Ser Trp Xaa Xaa Leu
1 5

<210> SEQ ID NO 10
<211> LENGTH: 6
<212> TYPE: PRT
<213> ORGANISM: Artificial Sequence
<220> FEATURE:
<223> OTHER INFORMATION: Peptide 5

<400> SEQUENCE: 10

Met Asn Val Ile Val Val
1 5

<210> SEQ ID NO 11
<211> LENGTH: 5
<212> TYPE: PRT
<213> ORGANISM: Artificial Sequence
<220> FEATURE:
<223> OTHER INFORMATION: Peptide

<400> SEQUENCE: 11

Gly Gly Asn Arg Gln
1 5

<210> SEQ ID NO 12
<211> LENGTH: 6
<212> TYPE: PRT
<213> ORGANISM: Artificial Sequence
<220> FEATURE:
<223> OTHER INFORMATION: Peptide

<400> SEQUENCE: 12

Met Ala Asp Arg Val Val 1 5

<210> SEQ ID NO 13
<211> LENGTH: 5
<212> TYPE: PRT
<213> ORGANISM: Artificial Sequence
<220> FEATURE:
<223> OTHER INFORMATION: Peptide

<400> SEQUENCE: 13

Glu Leu Lys Thr Thr
1 5

<210> SEQ ID NO 14
<211> LENGTH: 6
<212> TYPE: PRT
<213> ORGANISM: Artificial Sequence
<220> FEATURE:
<223> OTHER INFORMATION: Peptide

<400> SEQUENCE: 14

Arg Ala Glu Pro His Leu
1 5

<210> SEQ ID NO 15
<211> LENGTH: 5
<212> TYPE: PRT
<213> ORGANISM: Artificial Sequence
<220> FEATURE:
<223> OTHER INFORMATION: Peptide

<400> SEQUENCE: 15

Leu Asp Ser Ser Lys
1 5

<210> SEQ ID NO 16
<211> LENGTH: 26
<212> TYPE: DNA
<213> ORGANISM: Artificial Sequence
<220> FEATURE:
<223> OTHER INFORMATION: PCR Primer

<400> SEQUENCE: 16
ctgagggaca ccgtgtcggc gttcga 26

<210> SEQ ID NO 17
<211> LENGTH: 26
<212> TYPE: DNA
<213> ORGANISM: Artificial Sequence
<220> FEATURE:
<223> OTHER INFORMATION: PCR Primer

<400> SEQUENCE: 17
tcgaacgccg acacggtgtc cctcag 26

<210> SEQ ID NO 18
<211> LENGTH: 2400
<212> TYPE: DNA
<213> ORGANISM: Triticum aestivum

<400> SEQUENCE: 18
atgtcgtcgg cggtcgcgtc cgccgcatcc ttcctcgcgc tcgcgtcagc ctcccccggg 60
agatcacgca ggcgggcgag ggtgagcgcg cagccacccc acgccggggc cggcaggttg 120
cactggccgc cgtggccgcc gcagcgcacg gctcgcgacg gagctgtggc ggcgctcgcc 180

-continued

```
gccgggaaga aggacgcggg gatcgacgac gccgccgcgt ccgtgaggca gccccgcgca    240
ctccgcggtg gcgccgccac caaggtcgcg gagcgaaggg atcccgtcaa gacgctcgac    300
cgcgacgccg cggaaggcgg cgggccgtcc ccgccggcag cgaggcagga cgccgcccgt    360
ccgccgagta tgaacggcat gccggtgaac ggcgagaaca aatctaccgg cggcggcggc    420
gcgactaaag acagcgggct gcccacgccc gcacgcgcgc cccatccgtc gacccagaac    480
agagcaccgg tgaacggtga aaacaaagct aacgtcgcct cgccgccgac gagcatagcc    540
gaggccgcgg cttcggattc cgcagctacc atttccatca gcgacaaggc gccggagtcc    600
gttgtcccag ctgagaagac gccgccgtcg tccggctcaa atttcgagtc ctcggcctct    660
gctcccgggt ctgacactgt cagcgacgtg gaacaagaac tgaagaaggg tgcggtcgtt    720
gtcgaagaag ctccaaagcc aaaggctctt tcgccgcctg cagcccccgc tgtacaagaa    780
gacctttggg atttcaagaa atacattggt ttcgaggagc ccgtggaggc caaggatgat    840
ggccgggctg tcgcagatga tgcgggctcc tttgaacacc accagaatca cgactccgga    900
cctttggcag gggagaatgt catgaacgtg gtcgtcgtgg ctgctgagtg ttctccctgg    960
tgcaaaacag gtggtctggg agatgttgcg ggtgctctgc ccaaggcttt ggcaaagaga   1020
ggacatcgtg ttatggttgt ggtaccaagg tatggggact atgaagaagc ctacgatgtc   1080
ggagtccgaa aatactacaa ggctgctgga caggatatgg aagtgaatta tttccatgct   1140
tatatcgatg gagttgattt tgtgttcatt gacgctcctc tcttccgaca ccgtcaggaa   1200
gacatttatg gggcagcag acaggaaatt atgaagcgca tgattttgtt ctgcaaggcc    1260
gctgttgagg ttccatggca cgttccatgc ggcggtgtcc cttatgggga tggaaatctg   1320
gtgtttattg caaatgattg gcacacggca ctcctgcctg tctatctgaa agcatattac   1380
agggaccatg gtttgatgca gtacactcgg tccattatgg tgatacataa catcgctcac   1440
cagggccgtg gccctgtaga tgaattcccg ttcaccgagt tgcctgagca ctacctggaa   1500
cacttcagac tgtacgaccc cgtgggtggt gaacacgcca actacttcgc cgccggcctg   1560
aagatggcgg accaggttgt cgtggtgagc cccgggtacc tgtgggagct gaagacggtg   1620
gagggcggct gggggcttca cgacatcata cggcagaacg actggaagac ccgcggcatc   1680
gtcaacggca tcgacaacat ggagtggaac cccgaggtgg acgcccacct caagtcggac   1740
ggctacacca acttctccct gaggacgctg gactccggca agcggcagtg caaggaggcc   1800
ctgcagcgcg agctgggcct gcaggtccgc gccgacgtgc cgctgctcgg cttcatcggc   1860
cgcctggacg ggcagaaggg cgtggagatc atcgcggacg ccatgccctg gatcgtgagc   1920
caggacgtgc agctggtgat gctgggcacc gggcgccacg acctggagag catgctgcag   1980
cacttcgagc gggagcacca cgacaaggtg cgcgggtggg tggggttctc cgtgcgcctg   2040
gcgcaccgga tcacggcggg ggcggacgcg ctcctcatgc cctcccggtt cgagccgtgc   2100
gggctgaacc agctctacgc catggcctac ggcaccgtcc ccgtcgtgca cgccgtcggc   2160
ggcctcaggg acaccgtgcc gccgttcgac cccttcaacc actccgggct cgggtggacg   2220
ttcgaccgcg ccgaggcgca caagctgatc gaggcgctcg ggcactgcct ccgcacctac   2280
cgagacttca aggagagctg gagggccctc caggagcgcg gcatgtcgca ggacttcagc   2340
tgggagcacg ccgccaagct ctacgaggac gtcctcgtca aggccaagta ccagtggtga   2400
```

WHEAT STARCH AND WHEAT FLOURS AND FOODSTUFFS CONTAINING THESE WHEAT STARCH/WHEAT FLOURS

CROSS-REFERENCE TO RELATED APPLICATIONS

This is the U.S. National Stage application of International Patent Application No. PCT/EP2009/005098, filed Jul. 9, 2009, which claims priority to EP 08075631.5, filed Jul. 10, 2008, and U.S. Provisional Application No. 61/134,465, filed Jul. 10, 2008, the disclosures of each of which are hereby incorporated by reference in their entirety.

FIELD OF THE INVENTION

The present invention relates to wheat flours, the starch component whereof has an amylose content between 15.0 wt. % and 30.0 wt. % and which have a content of resistant starch of more than 5.0 wt. % and foodstuffs containing these wheat flours. Further, the present invention relates to methods for the production of said wheat flours and the use thereof as a prebiotic or for the production of foodstuffs with decreased glycemic index. The present invention also relates to nucleic acid molecules which code for a soluble starch synthase II, and vectors containing such nucleic acid molecules. Further the present invention also relates to host cells and plants which contain such nucleic acid molecules or vectors.

BACKGROUND OF THE INVENTION

The use of resistant starch (RS) is gaining increasing importance in the foodstuffs industry. Starch is mainly digested in the small intestine by the enzyme alpha amylase, which hydrolyzes the alpha-1,4-glucoside linkages of the starch to sugars. In contrast to this, resistant starch is not hydrolyzed in the small intestine by alpha amylases, but instead passes into the large intestine, where it behaves like roughage. From the degradation of RS-containing products, the body only obtains energy to a small extent. This energy input relates exclusively to the oxidative degradation of absorbed short-chain fatty acids from the large intestine. These short-chain fatty acids are end products of the carbohydrate metabolism of the intestinal microflora. With the uptake of RS-containing foodstuffs, substrates for the energy metabolism of the intestinal microflora and the large intestine epithelial cells are provided. For the maintenance of their structure and function, the latter are dependent on the luminal input of short-chain fatty acids and in particular of butyrate. Resistant starch is probably a factor for the prevention of diverticulosis and large intestine cancer.

A distinction is made between the following types of resistant starch:

- $RS_1$ Starch physically inaccessible to digestion, e.g. starch embedded in a protein or a fiber matrix. If this is broken down physically (e.g. by chewing) or chemically (e.g. by degradation of the matrix surrounding it), it can be processed by the digestive juices in the normal way.
- $RS_2$ Indigestible intact (granular) native starch granules, e.g. uncooked potato or banana starch, particularly from unripe bananas)
- $RS_3$ Indigestible retrograded starch, which is not granular
- $RS_4$ Indigestible chemically modified starch, e.g. by crosslinking or esterification (acetylation, etc.)

In contrast to RS 4, the RS forms 1 to 3 can be made accessible to alpha amylase degradation by dissolution in NaOH or Dimethyl sulfoxide.

For the production of resistant starch, various methods have been described. Most of these methods relate to the production of RS3 starches (EP 564893 A1; EP 688872 A1; EP 846704 A1; U.S. Pat. No. 5,051,271). All these methods for the production of resistant starch comprise the dispersion and gelatinization of starch in large excess quantities of water, followed by retrogradation with the use of enzymes or acids. They are based on the view that resistant starch is formed when the amylose fraction of starch retrogrades after the gelatinization of starch. It is assumed that after gelatinization the linear amylose molecules assemble into dense double-helix configurations bound by hydrogen bridge bonds, so that the alpha-1,4-glucoside linkages are no longer accessible to alpha amylases. These methods are labor-intensive, time-consuming and can result in low yields. Furthermore, the high water content of the products can render costly drying processes necessary.

Granular starches of the RS2 type with a high content of resistant starch are mainly found in native, uncooked, wild type potato starches which depending on the estimation method display an RS content between 74-85 wt. % (Faisant et al., Sciences des Aliments 15, (1995), 83-89; Evans and Thompson, Cereal Chemistry 81(1), (2004), 31-37).

Previously known granular maize starches with high RS content are always characterized by a high amylose content (>40 wt. %). For native, i.e. granular maize starches with high amylose content, which are synthesized in various maize plants of the amylose extender ("ae") genotype, RS values between about 40-70 wt. % were determined (Evans and Thompson, Cereal Chemistry 81(1), (2004), 31-37) by means of the RS estimation method of Englyst et al. (Europ. J. of Clinical Nutrition 46 (Suppl. 2), (1992), pp 33-50). The RS contents determined for native, i.e. granular amylomaize starch of the Hylon VII type (identical to ae VII, which was studied by Evans and Thompson) determined by Faisant et al. using two other RS estimation methods, at ca. 54 wt. % and 67 wt. % respectively, also lie in this range, which was also confirmed by a cross-laboratory study which, using different RS estimation methods, finds RS values for native amylomaize starch between about 50 and 72 wt. % (McCleary and Monaghan, J. AOAC Int. 85, (2002), 665-675). Such granular amylomaize starches from amylose extender (ae) mutants have the disadvantage of poor processing properties in certain product groups, since these starches hardly pregelatinize, and display low solubility and low swelling capacity. For applications in which only pregelatinized starches are usable or which require soluble starches or starches with swelling capacity, the amylomaize starches are thus either entirely unsuitable or they must be additionally chemically modified in order to fulfill these requirements, which is time- and cost-intensive (Senti and Russell, Tappi Vol. 43, No. 4, (April 1960), 343-349; Z. Luo et al., Starch/starch 58, (2006), 468-474).

Wheat starches with an increased RS content compared to wild type wheat plants have only recently become known and so far are only available to a very limited extent. The increased RS content of the previously known RS wheat starches is due to an increase in the amylose content, as with the amylomaize starches. In contrast to the ae mutants in maize, which are due to a mutation of the BEIIb gene from maize and have an amylose content between 50 and 90 wt. %, the increase in the amylose content necessary for raising the RS content is seen in wheat after inhibition of the gene expression of the branching enzymes IIa and IIb (Regina et al., PNAS Vol. 103 No. 10, (2006), 3546-3551). An alternative approach, which in wheat also leads to an increased amylose content and increased RS content of the wheat starch compared to the starch from wild type wheat plants, is based on the inhibition of the gene of soluble starch synthase IIa (SSIIa) (Yamamori et al., Australian Journal of Agricultural Research 57, (2006), 531-535). These SSIIa-inhibited wheat plants have a starch with an increased apparent amylose content, for which values of 37 wt. % (Yamamori et al., Australian Journal of Agricultural Research 57, (2006), 531-535) and 44 wt. % (Konik-Rose et al., Theor. Appl. Genet. 115, (2007), 1053-1065) were found. The increase in the apparent amylose content leads to an RS content of the native wheat starch of up to 3.6 wt. %, whereas native (granular) wheat starches from wild type plants contain little or no resistant starch (Yamamori et al., Australian Journal of Agricultural Research 57, (2006), 531-535). The wheat flour of these SSIIa-inhibited wheat plants leads on baking to an undesired diminution in the bread volume (Morita et al., Cereal Chemistry 79, (2002), 491-495) and the dough produced from the wheat flour displays decreased dough stability (Morita et al., Cereal Chemistry 79, (2002), 491-495; Hung et al., Cereal Chemistry 82, (2005), 690-694; Hung et al., Trends in Food Science & Technology 17, (2006), 448-456). The experts assume that an increase in the RS content of wheat starches or flours can be achieved by increasing the apparent amylose content (Morell et al., Journal of AOAC International Vol. 87 No. 3, (2004), 740-748; Yamamori et al., Australian Journal of Agricultural Research 57, (2006), 531-535).

Apart from resistant starches (RS), there is also increasing demand in foodstuffs production for starches or flours with a low content of rapidly digestible starch (rapidly digestible starch=RDS), since there is a suspicion that the continual consumption of foodstuffs with a high glycemic loading, such as for example in conventional starch-containing foodstuffs of relatively high RDS content, and the insulin release associated therewith is a risk factor in the onset of diseases such as hypertension, overweight, heart disease and type II diabetes. As a rule, foods of high RDS content have a high glycemic index (=GI) (Englyst et al., British Journal of Nutrition, 75, 327-337).

The rapid release of rather large quantities of glucose to be observed in the digestion of conventional starches/flours or of processed products from these starches/flours (e.g. bakery products and noodles) and the absorption thereof via the small intestine epithelium leads to an abrupt increase in the blood sugar level and to an outpouring of insulin (insulin response). If the RDS content of a starch or flour is decreased, then this leads to a retarded release of glucose from the starch, to a modified insulin response and hence finally to a decrease in the risk of the aforesaid diseases.

The use of wheat starches and flours with a low content of RDS appears desirable above all in those foods where the aim is a continuous release of glucose, such as for example in sports foods for endurance sports or in dietary foods to reduce the feeling of hunger.

SUMMARY OF PREFERRED EMBODIMENTS OF THE INVENTION

Figure 1:
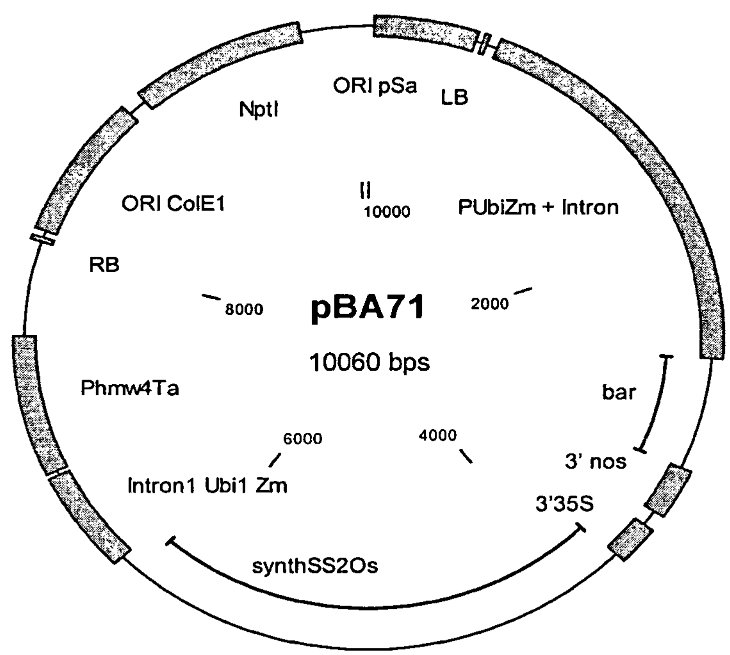
FIG. 1 shows a vector map of the pBA71 genetic components transferred into the plant genome.

The purpose of the present invention is thus to provide wheat flours/wheat starches which have modified digestive properties compared to wheat flours/wheat starches from wild type wheat plants, in particular an increased content of resistant starch (RS) and/or a decreased content of rapidly digestible starch (RDS).

A further purpose of the present invention is to provide wheat flours or wheat starches which as well as the modified digestive properties have processing properties which are improved compared to the processing properties of the wheat flours/wheat starches with increased amylose content described in the state of the art. Among improved processing properties in this connection, for example increased bread volume of the loaves and/or increased dough stability and/or increased thermal stability can be mentioned.

These problems are solved by the embodiments described in the claims.

DETAILED DESCRIPTION OF PREFERRED EMBODIMENTS OF THE INVENTION

The present invention thus relates to a wheat starch which has an amylose content between 15.0 wt. % and 30.0 wt. %, preferably between 18.0 wt. % and 30.0 wt. % and particularly preferably between 20.0 wt. % and 30.0 wt. % and which has a content of resistant starch (RS starch) (English: resistant starch, abbreviated RS) of more than 5.0 wt. %, preferably between 5.0 wt. % and 35.0 wt. %, particularly preferably between 7.0 wt. % and 30 wt. %.

In this connection and in connection with the present invention, the term "between" is not intended to include the respective numerical limits stated.

Since the state of the art assumes that an increase in the RS content of wheat starches or flours can be achieved by an increase in the apparent amylose content (Morell et al., Journal of AOAC International Vol. 87 No. 3, (2004), 740-748; Yamamori et al., Australian Journal of Agricultural Research 57, (2006), 531-535), it is very surprising to the person skilled in the art that the wheat starches/flours according to the invention exhibit a markedly increased RS content compared to starches/flours from wild type wheat plants with almost unchanged or even slightly decreased apparent amylose content.

In a further embodiment, the present invention relates to a wheat starch which has an amylose content between 15.0 wt. % and 30.0 wt. %, preferably between 18.0 wt. % and 29.5 wt. % and particularly preferably between 20.0 wt. % and 29.5 wt. % and a content of resistant starch (RS starch) (English: resistant starch, abbreviated RS) of more than 5.0 wt. %, preferably between 5.0 wt. % and 15.0 wt. % or between 16.0 wt. % and 29.0 wt. %.

The present invention also relates to a wheat starch which has an amylose content between 15.0 wt. % and 30.0 wt. %, preferably between 18.0 wt. % and 30.0 wt. % and particularly preferably between 20.0 wt. % and 30.0 wt. % and which has a content of rapidly digestible starch (English: rapidly digestible starch=RDS starch) between 10.0 wt. % and 38 wt. %, preferably between 15.0 wt. % and 35.0 wt. %, particularly preferably between 20.0 wt. % and 33 wt. %.

In a further embodiment, the present invention relates to a wheat starch which has a content of rapidly digestible starch (English: rapidly digestible starch=RDS) between 10.0 wt. % and 38 wt. %, preferably between 15.0 wt. % and 35.0 wt. %, particularly preferably between 20.0 wt. % and 33 wt. %.

In a further embodiment, the wheat starch according to the invention has an RS content (RS starch) between 5.0 wt. % and 35.0 wt. %, preferably between 7.0 wt. % and 32 wt. %, particularly preferably between 10 wt. % and 30.0 wt. %.

Methods for the determination of the amylose content are known to the person skilled in the art. Some of these methods are based on the iodine-binding capacity of the amylose, which can be estimated potentiometrically (Banks & Greenwood, in W. Banks & C. T. Greenwood, Starch and its components (pp. 51-66), Edinburgh, Edinburgh University Press), amperometrically (Larson et al., Analytical Chemistry 25(5), (1953), 802-804) or spectrophotometrically (Morrison & Laignelet, J. Cereal Sc. 1, (1983), 9-20). The determination of the amylose content can also be effected calorimetrically by DSC (Differential Scanning calorimetry) measurements (Kugimiya & Donovan, Journal of Food Science 46, (1981), 765-770; Sievert & Holm, Starch/Stärke 45 (4), (1993), 136-139). There is also the possibility of determining the amylose content by the use of SEC (size exclusion chromatography) chromatography of native or debranched starch.

In connection with the present invention, the amylose content of the starch component of the wheat flour according to the invention is determined by means of the DSC method "determination of the content of apparent amylose" described later. The DSC method can here be performed on a wheat starch sample (a method for the isolation of wheat starch from wheat flour is described later under "Preparation of wheat flour and subsequent extraction of wheat starch") or on a wheat flour sample.

Preferably the DSC method is performed on a wheat flour sample (for the production of the wheat flour, see "Preparation of wheat flour and subsequent extraction of wheat starch"). The amylose content of the starch is then obtained—assuming an x % content by weight of the starch in a wheat flour sample (Hung et al., Trends in Food Science & Technology 17, (2006), 448-456)—by calculation according to the following formula:

$$\text{Amylose content of the starch} = \frac{\text{amylose content (flour)} \times 100}{x}$$

The content by weight of the starch in the flour sample is preferably determined in the manner described in Method 8 (determination of the content of rapidly digestible and resistant starch in wheat flours/starches).

In connection with the present invention, the determination of the RS content of the starch (RS starch) is preferably performed by the method of Englyst et al. (Europ. J. of Clinical Nutrition 46 (Suppl. 2), (1992), pp 33-50, see in particular the following paragraphs from Englyst et al., page 35-36: "Reagents, Apparatus, Spectrophotometer"; page 36-37, Section "Measurement of free glucose (FG)"; and page 38, Section "Measurement of RDS and SDS"). The percentage of the weighed out flour sample (fresh weight) which is not released as glucose after 2 hrs in the method described is described as the resistant starch content of the starch (RS starch). It is thus obtained according to the following formula:

RS starch as % of total starch=100%−100%×(glucose released after 2 hrs in mg/total starch in mg)

The total starch content is preferably determined in the manner described in Method 8 (determination of the content of rapidly digestible and resistant starch in wheat flours/starches).

In connection with the present invention, "the content of rapidly digestible starch (RDS)" (=Rapidly Digestible Starch=RDS starch) should be understood to mean the percentage of a wheat starch which is released as glucose after 20 minutes in the aforesaid method of Englyst et al. for the determination of the RS content. The RDS starch content is stated in weight percent of the total starch. Hence, in connection with the present invention the following applies:

RDS starch in % total starch=100%×released glucose after 20 minutes in mg/total starch in mg The total starch content is preferably determined in the manner described in Method 8 (determination of the content of rapidly digestible and resistant starch in wheat flours/starches).

The thermal properties of the wheat starch according to the invention and the wheat flour according to the invention can by analyzed by the heat flow calorimetry method (Differential Scanning calorimetry=DSC). These are presented as the gelatinization temperature with the values for DSC T-onset (=lowest gelatinization temperature) and for DSC T-peak (=highest gelatinization temperature).

In connection with the present invention, the term "DSC T-onset temperature" should be understood to mean that temperature which represents the start of the phase conversion of the starch or flour sample. It is characterized as the intersection point between the extension of the baseline and the tangent laid onto the rising flank of the peak through the inflexion point.

In connection with the present invention, the term "DSC T-peak temperature" designates the temperature at which the DSC curve of the starch or flour sample has reached a maximum and the first derivative of the curve is zero.

In connection with the present invention, the determination of the "DSC T-onset" and "DSC T-peak" temperature is effected by the method described below ("Thermal analysis of flour/starch by the heat flow calorimetry method (Differential Scanning Calorimetry").

In a further embodiment, the present invention relates to a wheat starch which has an amylose content between 15.0 wt. % and 30.0 wt. %, preferably between 18.0 wt. % and 30.0 wt. % and particularly preferably between 20.0 wt. % and 30.0 wt. % and which has a DSC T-onset temperature between 63.0° C. and 70.0° C., preferably between 64.0° C. and 69.0° C., particularly preferably between 65.0° C. and 68.0° C.

In a further embodiment, the present invention relates to a wheat starch which has an amylose content between 15.0 wt. % and 30.0 wt. %, preferably between 18.0 wt. % and 30.0 wt. % and particularly preferably between 20.0 wt. % and 30.0 wt. % and which has a DSC T-peak temperature between 70.0° C. and 78.0° C., preferably between 71.0° C. and 75.0° C.

In a further embodiment, the wheat starch according to the invention has a DSC T-peak temperature between 71.0° C. and 77.0° C., preferably between 72.0° C. and 75.0° C.

In a further embodiment, the present invention relates to a wheat starch which as well as an amylose content between 15.0 wt. % and 30.0 wt. %, preferably between 18.0 wt. % and 29.5 wt. % and particularly preferably between 20.0 wt. % and 29.5 wt. % in addition optionally has a) an RS content between 5.0 wt. % and 30.0 wt. %, preferably between 6.0 wt. % and 29.5 wt. %, particularly preferably between 7 wt. % and 29.5 wt. %; and/or b) a content of rapidly digestible starch (English: rapidly digestible starch=RDS) based on the quantity of starch (dry weight) between 10.0 wt. % and 38 wt. %, preferably between 15.0 wt. % and 35.0 wt. %, particularly preferably between 20.0 wt. % and 33 wt. %; and/or c) a DSC T-onset temperature between 63.0° C. and 70.0° C., preferably between 64.0° C. and 69.0° C., particularly preferably between 65.0° C. and 68.0° C.; and/or d) a DSC T-peak temperature between 70.0° C. and 78.0° C., preferably between 71.0° C. and 75.0° C.

In a further embodiment, the wheat starch according to the invention has a modified side-chain distribution of the side-chains of the amylopectin compared to the side-chain distribution of the amylopectin of wild type wheat starch.

In a further embodiment, the wheat starch according to the invention exhibits an increase in the proportion of the side-chains of the amylopectin with a degree of polymerization (DP) of DP 17-20 by 2%-20%, preferably by 5%-15%, compared to the proportion of the corresponding side-chains of the amylopectin of corresponding wild type wheat plants.

In a further embodiment, the wheat starch according to the invention exhibits a decrease in the proportion of the side-chains of the amylopectin with a degree of polymerization (DP) of DP 6-11 by 5%-50%, preferably by 10%-15%, compared to the proportion of the corresponding side-chains of the amylopectin of corresponding wild type wheat plants.

In a further embodiment, the wheat starch according to the invention has an ACR value of less than 0.160, preferably of less than 0.155.

In connection with the present invention, the ACR value is understood to mean the ratio of the sum of the proportions of the side-chains with DP 6-10 divided by the sum of the proportions of the side-chains with DP 6-24.

In connection with the present invention, the determination of the side-chain distribution is effected by the method described later ("Preparation of wheat flour/starch for the study of the amylopectin side-chain distribution by high pressure ion exchange chromatography"). The determination of the proportion of side-chains is effected via the determination of the percentage content of a certain side-chain in the total content of all side-chains. The total content of all side-chains is determined via the determination of the total area under the peaks which represent the degrees of polymerization from DP 6 to 50 in the HPLC chromatogram. The percentage content of a certain side-chain in the total content of all side-chains is determined by the determination of the ratio of the area under the peak which this side-chain represents in the HPLC chromatogram to the total area. For the determination of the peak areas, the program Chromelion 6.60 from the firm Dionex, USA can for example be used.

In a particularly preferable embodiment of the present invention, the wheat starches according to the invention are granular wheat starches.

In a further particularly preferable embodiment of the present invention, the wheat flours according to the invention are wheat flours the starch component whereof, i.e. the wheat starch according to the invention, is granular.

In connection with the present invention, a "granular wheat starch" should be understood to mean a wheat starch which has not or not completely been pregelatinized and mainly has a granular structure, i.e. at least 90%, preferably at least 95%, particularly preferably at least 99% of the starch grains of a starch sample have a granular shape. Completely retrograded wheat starch is not a granular wheat starch in the sense of the present invention. In the optical microscope under polarized light, the granular structure of wheat starch grain leads to a characteristic optical double refraction and is determinable thereby (see for example page 126, FIG. 4 in Yahl et al., Microscope 32, (1984), 123-132).

In a further embodiment, the present invention relates to the use of the wheat starch according to the invention, which is preferably a granular wheat starch, as resistant starch.

In a further embodiment, the present invention relates to the use of the wheat starch according to the invention, which is preferably a granular wheat starch, as a prebiotic, since the wheat starch according to the invention surprisingly displays an increased RS content compared to wheat starch from wild type wheat plants. Hitherto, a prebiotic effect could only be demonstrated for wheat starches with an increased amylose content (Regina et al., PNAS Vol. 103 No. 10, (2006), 3546-3551).

In addition, the wheat flours/wheat starches according to the invention have the advantage of a decreased content of rapidly digestible flour or starch (RDS), which is particularly advantageous since a rapid release of rather large quantities of glucose and its absorption via the small intestine epithelium leads to an abrupt increase in the blood sugar level. As a result of this there is an outpouring of insulin (insulin response). The continual consumption of foodstuffs with a high glycemic loading, and the insulin outpouring connected therewith, are suspected of being a risk factor in the onset of diseases such as hypertension, overweight, heart disease and type II diabetes.

In a further embodiment, the present invention therefore relates to the use of the wheat starch according to the invention, which is preferably a granular wheat starch, or of the wheat flour according to the invention described below for the production of a foodstuff, preferably one for the nutrition of diabetics or a foodstuff suitable for the prevention of hypertension, overweight, heart disease or type II diabetes. On the basis of the replacement of conventional wheat starch or wheat flour, e.g. from wild type wheat plants, by the wheat starch according to the invention or the wheat flour according to the invention, the foodstuff preferably displays a reduced glycemic index, which is attributable to the fact that the wheat starch according to the invention/the wheat flour according to the invention contains a markedly reduced content of rapidly digestible starch (=RDS starch) or rapidly digestible flour (=RDS flour) compared to starch/flour from wild type wheat plants.

In a further embodiment, the present invention relates to the use of the—preferably granular—wheat starch according to the invention or the wheat flour according to the invention as a component of diabetic food or for the prevention of hypertension, overweight, heart disease or type II diabetes.

In a further embodiment, the present invention also relates to the use of the—preferably granular—wheat starch according to the invention or the wheat flour according to the invention for the production of foodstuffs which have a decreased glycemic index compared to the glycemic index of foodstuffs which contain starch or flour from wild type wheat plants.

In a further embodiment, the present invention relates to the use of the—preferably granular—wheat starch according to the invention or the wheat flour according to the invention for decreasing the glycemic index of foodstuffs compared to the glycemic index of foodstuffs which contain starch or flour from corresponding wild type wheat plants.

The glycemic index (=GI) is a measure for the determination of the action of a carbohydrate-containing foodstuff on the blood sugar level. The glycemic index states numerically the blood sugar-increasing action of the carbohydrate or the foodstuffs. The blood sugar-increasing action of grape sugar (=glucose) or white bread is as a rule used as a reference value here (100).

In order to determine the GI of a foodstuff, the variation in the blood sugar with time is measured in test persons after a meal, as a rule over a period of 2 hours. For this, the subjects received the food whose GI is to be established in a quantity which contains exactly 50 grams of utilizable carbohydrates. After the "test meal", the blood sugar is measured regularly and the variation therein thus observed. The measurement is performed on several test persons, and a mean value is calculated in order to take account of the blood sugar curves appearing differently from person to person. The areas under the blood sugar curves are integrated. The area which results after the uptake of glucose (normally 50 grams) (=reference foodstuff) is set at 100 as the standard. The GI for a foodstuff thus describes the relative area under the blood sugar curve as a percentage value compared to the curve after the reference foodstuff (glucose).

Detailed method descriptions for the determination of the glycemic index are known to the person skilled in the art and for example described by Wolever et al. (Am. J. Clin. Nutr. 54, (1991), 846-854) or in FAO Food and Nutrition Paper. 66, "Carbohydrates in human nutrition", Chapter 4—The Role of the Glycemic Index in Food Choice, pp. 25-30, Report from Apr. 14-18, (1997).

A higher GI means that the carbohydrates of the foodstuff are rapidly degraded to glucose and pass into the blood, so that the blood sugar level rises rapidly and a strong, regulative insulin outpouring takes place. In contrast, foodstuffs with a medium or low GI cause only a slower and overall smaller rise in the blood sugar curve.

In a further embodiment, the present invention relates to the use of the—preferably granular—wheat starch according to the invention or the wheat flour according to the invention for the production of foodstuffs which after uptake by the human body lead to a slower rise in the blood sugar level than is the case after uptake of corresponding foodstuffs which contain starch/flour from (corresponding) wild type wheat plants.

Compared to the previously known wheat starches/wheat flours, the wheat starches/wheat flours according to the invention further have the advantage that as well as a lower content of RDS compared to wheat wild type starches/wild type flours they simultaneously display an increased content of RS. The advantages associated with this increase in the RS content of the starch/flour, such as for example the prebiotic action, are thus paired with the advantages, which are attributable to the reduced RDS content of the starch/flours (e.g. decreased glycemic response).

Typical foodstuffs to which the starch according to the invention/flour according to the invention can be added or which can be produced from the wheat starches/wheat flours according to the invention, include tortillas, tortilla chips, bakery products (e.g. bread, wheat bread, rolls, cookies, cakes, waffles, muffins, unleavened wheat cakes, bagels), pancakes, pizzas, pasta (e.g. noodles), stews, sauces, wheat flour pudding, dairy products (e.g. yoghurt, curd cheese), puddings, spreads (e.g. butter, margarine), drinks, powdered drinks, ready-to-serve meals, dressings, (breakfast) cereals and the like.

In a further embodiment, the present invention relates to a method for the production of a—preferably granular—wheat starch according to the invention comprising the step of extraction of the starch according to the invention from a wheat plant which expresses a heterologous starch synthase II.

In a further embodiment the present invention further relates to a method for the production of a starch, comprising the step of extraction of the starch from a wheat plant cell which expresses a heterologous starch synthase II.

In a preferred embodiment of the present invention, the wheat starch according to the invention is extracted from a wheat plant according to the invention containing wheat plant cells according to the invention, from propagative material according to the invention of a wheat plant according to the invention and/or from starch-storing parts of a wheat plant according to the invention.

Preferably, the method according to the invention also comprises the step of harvesting the cultivated wheat plant or the starch-storing plant parts according to the invention and/or the propagative material according to the invention of the wheat plant according to the invention before the extraction of the starch. In a further embodiment, the method according to the invention also comprises the step of cultivation of the wheat plant according to the invention before the harvesting.

Methods for the extraction of the starch from plants or from starch-storing parts of wheat plants are known to the person skilled in the art. Further, methods for the extraction of the starch from wheat plants are described, e.g. in Starch: Chemistry and Technology (Eds.: Whistler, BeMiller and Paschall (1994), 2nd Edition, Academic Press Inc. London Ltd; ISBN 0-12-746270-8; see e.g. Chapter XV, page 491 to 506: wheat starch: production, modification and uses; or in Eckhoff et al., Cereal Chem. 73 (1996), 54-57). Devices which are normally used for the extraction of starch from plant material are separators, decanters, hydrocyclones, spray driers and fluidized bed driers.

In connection with the present invention, the term "starch-storing parts" should be understood to mean those parts of a plant in which, in contrast to transitory leaf starch, starch is stored as a depot for survival over longer time periods. Preferred starch-storing plant parts are wheat grains, and particularly preferred are wheat grains containing an endosperm.

Further, the present invention also relates to wheat plant cells or wheat plants which express a heterologous starch synthase II.

In a preferred embodiment, the wheat plant cells or wheat plants according to the invention synthesize the wheat starch according to the invention.

In connection with the present invention, the term "starch synthase II" should be understood to mean a protein which catalyses a glucosylation reaction wherein glucose residues of the substrate ADP-glucose are transferred onto alpha-1,4-linked glucan chains with formation of an alpha-1,4 linkage (ADP-glucose+{(1,4)-alpha-D-glucosyl}(N)<=>ADP+{(1,4)-alpha-D-glucosyl}(N+1)). The amino acid sequence of starch synthase II displays an identity of at least 86%, preferably at least 93%, particularly preferably at least 95% with the amino acids 333 to 362 (domain 1) of the amino acid sequence presented under SEQ ID No.4 and/or an identity of at least 83%, preferably at least 86%, particularly preferably at least 95% with the amino acids 434 to 473 (domain 2) of the amino acid sequence presented under SEQ ID No.4 and/or an identity of at least 70%, preferably at least 82%, preferably 86%, particularly preferably 98%, especially preferably of at least 95% with the amino acids 652 to 716 (domain 3) of the amino acid sequence presented under SEQ ID No.4.

In a preferred embodiment of the present invention, the starch synthase II has at least one, preferably two, of the following peptide moieties:

PWHAVGGLRDTV (SEQ ID No.7) and/or additionally either the moiety SWXXI (SEQ ID No.8) or SWXXL (SEQ ID No.9).

In a preferred embodiment of the present invention, the starch synthase II additionally has one or more of the following peptide moieties: MNVIW (SEQ ID No.10), GGNRQ (SEQ ID No 11), MADRW (SEQ ID No.12), ELKTT (SEQ ID No.13), RAEPHL (SEQ ID No.14), LDSSK (SEQ ID No.15).

Nucleic acid sequences and the amino acid sequences corresponding thereto which have the required identity with the domains 1, 2 and 3 and which code for a starch synthase II are known to the person skilled in the art and for example published by Gao and Chibbar, (Genome 43 (5), (2000), 768-775: starch synthase II from wheat NCBI Acc No. AJ269502.1, AJ269503.1, AJ269504.1) or under access No. AF155217.2

(*Triticum aestivum*), AY133249 (*Hordeum vulgare*), access No. AY133248 (*Aegilops tauschii*), access Nos. XP467757, AAK64284 (*Oryza sativa*), access No. AAK81729 (Oryza sativa) access Nos. AAD13341 and AAS77569, access No. AAF13168 (*Manihut esculenta*), access No. AAP41030 (*Colocasia esculenta*), access No. AAS88880 (*Ostraeococcus taun*), or access No. AAC17970 (*Chlamydomonas reinhardii*). Said nucleic acid sequences and amino acid sequences coding for a protein with the activity of a starch synthase II are accessible via NCBI website (world wide web at ncbi.nlm.nih.gov/entrez/) and by mention of the references are expressly included in the disclosure content of the present application.

In connection with the present invention, a "heterologous starch synthase II" should be understood to mean a starch synthase II the coding nucleotide sequence whereof does not occur naturally in the wheat plant (cell) or which is not under the control of its own promoter, and/or the coding DNA sequence whereof is for example introduced into the wheat cell by genetic engineering methods, such as for example transformation of the cell. Preferably, the heterologous starch synthase is derived from a different plant species than the transformed wheat plant cell or wheat plant. Particularly preferably, the coding DNA sequence of the heterologous starch synthase II is derived from a different plant genus than the transformed wheat plant cell or plant.

In connection with the present invention, the term "plant genus" should be understood to mean a hierarchical level of biological systematics. A genus contains one or more species. An example of genus is *Triticum* L. (Wheat). All species within a genus always have a two-part (binominal) name, which in addition to the genus designation also contains a species epitheton. *Triticum aestivum* L. (soft wheat) is thus a species of the genus *Triticum*.

In a particularly preferable embodiment, a heterologous starch synthase II from the genus *Oryza*, preferably the species *Oryza sativa* is used in connection with the present invention. Also preferred is the starch synthase II which is designated by Jiang et al. as OsSSII-3 (Jiang H., Dian W., Liu F., Wu P. (2004). Molecular cloning and expression analysis of three genes encoding starch synthase II in rice. Planta, 218, 1062-1070; GenBank Acc. No. AF419099.1=SEQ ID No.1). Particularly preferable is a starch synthase II which compared to OsSSII-3 (SEQ ID No.2) exhibits an amino acid exchange (valine in place of a methionine) at position 737 of the amino acid sequence stated under SEQ ID No.2 and the complete amino acid sequence whereof is stated under SEQ ID No.4.

Preferably, the starch synthase II has the nucleotide sequence stated under SEQ ID No.1. Particularly preferably, the starch synthase II has the nucleotide sequence stated under SEQ ID No.3. SEQ ID No.3 differs from SEQ ID No.1 by a nucleotide exchange at position 2209 of the nucleotide sequence stated under SEQ ID No.1 (adenine replaced by guanine). Particularly preferably, the starch synthase II is with the nucleotide sequence stated under SEQ ID No.3.

In a further preferred embodiment, a synthetic starch synthase II is used in connection with the present invention. Particularly preferred is a synthetic variant of starch synthase II which has the nucleotide sequence stated under SEQ ID No.5. In contrast to the natural starch synthase II from wheat which is stated under SEQ ID No.6 and which codes for the same protein as SEQ ID No.5, the synthetic sequence of SEQ ID No.5 was optimized by nucleotide exchanges, in order to achieve as strong as possible an increase in the SSII activity compared to wild type wheat plants.

The present invention thus also relates to a nucleic acid molecule coding for a protein with the enzymatic activity of a starch synthase II, the nucleic acid molecule being selected from the group consisting of (a) a nucleic acid molecule which codes for a protein which includes the amino acid sequence stated under Seq ID NO.4;
(b) a nucleic acid molecule which the nucleotide sequence presented under Seq ID No.3 or a ribonucleotide sequence corresponding hereto;
(c) a nucleic acid molecule which the nucleotide sequence presented under Seq ID No.5 or a ribonucleotide sequence corresponding hereto;
(d) a nucleic acid molecule, whereof the nucleotide sequence owing to the degeneracy of the genetic code deviates from the sequence of a nucleic acid molecule mentioned under (a) or (b).

In a further embodiment, the present invention relates to vectors, in particular plasmids, cosmids, viruses, bacteriophages and other vectors common in genetic engineering, which contain the nucleic acid molecules according to the invention.

In a further embodiment, the nucleic acid molecules according to the invention contained in the vectors are linked with control sequences which initiate expression in prokaryotic or eukaryotic cells. Here, the term "expression" can mean transcription and also transcription and translation. Preferably here, the nucleic acid molecules according to the invention lie before the control sequences in "sense" orientation.

A further subject of the present invention is a host cell, in particular a prokaryotic or eukaryotic cell (it not being intended that human cells be covered by this term) which is genetically modified with a nucleic acid molecule according to the invention and/or with a vector according to the invention, and cells which are derived from such host cells and which contain the genetic modification according to the invention.

In a further embodiment, the invention relates to host cells, in particular prokaryotic or eukaryotic cells (it not being intended that human cells be covered by this term) which have been transformed with a nucleic acid molecule according to the invention or a vector according to the invention, and host cells which are derived from such host cells and contain the described nucleic acid molecules or vectors according to the invention.

The host cells can be bacterial (e.g. *E. coli*, bacteria of the genus *Agrobacterium* in particular *Agrobacterium tumefaciens* or *Agrobacterium rhizogenes*) or fungal cells (e.g. yeast, in particular *S. cerevisiae, Agaricus*, in particular *Agaricus bisporus, Aspergillus, Trichoderma*), and plant or animal cells. Here, the term "transformed" means that the cells according to the invention are genetically modified with a nucleic acid molecule according to the invention insofar as in addition to their natural genome they contain at least one nucleic acid molecule according to the invention. This can be present in the cells free, optionally as a self-replicating molecule, or it can be present stably integrated into the genome of the host cell.

Preferably, the host cells are microorganisms. In the context of the present application, this is understood to mean all bacteria and all protists (e.g. fungi, in particular yeasts and algae), as for example defined in Schlegel "General Microbiology" (Georg Thieme Verlag (1985), 1-2).

Preferably, the host cells according to the invention are plant cells. These can in principle be plant cells from any plant species, i.e. both monocotyledonous and also dicotyledonous plants. They are preferably plant cells from agriculturally useful plants, i.e. from plants which are cultivated by man for food purposes or for technical, in particular industrial, purposes. Preferably the invention relates to plant cells and plants from starch-storing plants (maize, rice, wheat, rye, oats, barley, manioc, potato, sago, mung bean, pea or sorghum), preferably plant cells from plants of the (systematic) family Poacea. Particularly preferable are plant cells from wheat plants.

In connection with the present invention, the term "identity" should be understood to mean the number of amino acids/nucleotides coinciding (identity) with other proteins/nucleic acids, expressed in percent. Preferably, the identity of a protein with the activity of a starch synthase II is determined by comparison with the amino acid sequence stated under SEQ ID No.4 or the identity of a nucleic acid molecule coding for a protein with the activity of a starch synthase II by comparison with the nucleic acid sequence stated under SEQ ID No.3 with other proteins/nucleic acids by computer programs. If sequences which are being compared with one another have different lengths, the identity should be determined such that the number of amino acids/nucleotides which the shorter sequence has in common with the longer sequence determines the percentage proportion of the identity. Preferably the identity is determined by means of the known and publicly available computer program ClustalW (Thompson et al., Nucleic Acids Research 22 (1994), 4673-4680). ClustalW is made publicly available by Julie Thompson and Toby Gibson, European Molecular Biology Laboratory, Meyerhofstrasse 1, D 69117 Heidelberg, Germany. ClustalW can also be downloaded from various internet sites, inter alia at IGBMC (Institut de Genetique et de Biologie Moleculaire et Cellulaire, B.P.163, 67404 Illkirch Cedex, France and at EBI and at all mirrored internet sites of the EBI (European Bioinformatics Institute, Wellcome Trust Genome Campus, Hinxton, Cambridge CB10 1SD, UK).

Preferably, the ClustalW computer program Version 1.8 is used to determine the identity between proteins described in the context of the present invention and other proteins. For this, the following parameters should be set: KTUPLE=1, TOPDIAG=5, WINDOW=5, PAIRGAP=3, GAPOPEN=10, GAPEXTEND=0.05, GAPDIST=8, MAXDIV=40, MATRIX=GONNET, ENDGAPS(OFF), NOPGAP, NOHGAP. Preferably, the ClustalW computer program Version 1.8 is used to determine the identity between e.g. the nucleotide sequence of the nucleic acid molecules described in the context of the present invention and the nucleotide sequence of other nucleic acid molecules. For this, the following parameters should be set: KTUPLE=2, TOPDIAGS=4, PAIRGAP=5, DNAMATRIX:IUB, GAPOPEN=10, GAPEXT=5, MAXDIV=40, TRANSITIONS: unweighted.

In a further embodiment of the present invention, the wheat plant (cell) which synthesizes the wheat starch according to the invention is genetically modified, the genetic modification leading to an increase in the activity of a starch synthase II compared to corresponding non genetically-modified wild type wheat plant cells or wild type wheat plants.

Here, the genetic modification can be any genetic modification which leads to an increase in the activity of a starch synthase II compared to corresponding non genetically-modified wild type wheat plant cells or wild type wheat plants.

In connection with the present invention, the term "wild type wheat plant cell" means that these are wheat plant cells which served as starting material for the production of the wheat plant cells according to the invention which synthesize the starch according to the invention.

In connection with the present invention, the term "wild type wheat plant" means that these are wheat plants which were used as the starting material for the production of the wheat plants according to the invention which synthesize the starch according to the invention.

Preferably, the term "wild type wheat plant" relates to the variety Fielder, which is publicly available, for example at the Alberta Stock Seed Distribution Committee, Alberta Agriculture and Rural Development, J. G. O'Donoghue Building 203, 7000-113 St. Edmonton, AB T6H 5T6, Canada.

In connection with the present invention, the term "corresponding" means that in the comparison of several articles, the relevant articles which are compared with one another are kept under the same conditions. In connection with the present invention, the term "corresponding" in connection with wild type wheat plant cells or wild type wheat plants means that the plant cells or plants which are compared with one another were grown under the same cultivation conditions and that they have an equal (cultivation) age.

In the context of the present invention, the term "increase in the activity of a starch synthase II" means an increase in the expression of endogenous genes which code for proteins with the activity of a starch synthase II and/or an increase in the quantity of proteins with the activity of a starch synthase II in the wheat plant (cells) and/or preferably an increase in the enzymatic activity of proteins with the activity of a starch synthase II in the wheat plant (cells) according to the invention.

The increase in expression can for example be determined by measurement of the quantity of transcripts which code for proteins with the activity of a starch synthase II. The determination can for example be effected by Northern blot analysis or RT-PCR.

The quantity of the activity of a protein with the activity of a starch synthase II can for example be determined as described in the literature (Nishi et al., 2001, Plant Physiology 127, 459-472). A method for the determination of the quantity of activity of a protein with the activity of a starch synthase II preferred in connection with the present invention is described later ("Determination of SSII activity using activity gel").

Preferably, the wheat plant (cells) which synthesize the starch according to the invention have an enzymatic activity of the starch synthase II which is increased at least 2-fold, preferably 3 to 10-fold compared to corresponding non genetically-modified wild type wheat plant cells or wild type wheat plants.

In a further embodiment of the present invention, the genetic modification of the wheat plant (cell) according to the invention consists in the introduction of at least one foreign nucleic acid molecule into the genome of the plant cell or into the genome of the plant.

In this connection, the term "genetic modification" means the introduction of at least one foreign nucleic acid molecule into the genome of a wheat plant (cell), where said introduction of this molecule leads to the increase in the activity of a protein with the activity of a starch synthase II.

Through introduction of a foreign nucleic acid molecule, the wheat plants (cells) according to the invention are modified in their genetic information. The presence or the expression of at least one foreign nucleic acid molecule leads to a phenotypic modification. Here, "phenotypic modification" preferably means a measurable modification of one or more functions of the cell. For example, owing to the presence or on expression of introduced foreign nucleic acid molecules, the genetically modified wheat plant (cells) display an increase in the activity of a protein with the activity of a starch synthase II and/or synthesize a wheat starch according to the invention.

In connection with the present invention, the term "foreign nucleic acid molecule" is understood to mean such a molecule which either does not occur naturally in corresponding wild type wheat plant (cells) or which does not occur naturally in the specific spatial disposition in wild type plant (cells) or which is localized at a site in the genome of the wild type plant cell at which it does not occur naturally. In principle, a foreign nucleic acid molecule can be any nucleic acid molecule which causes an increase in the activity of a protein with the activity of a starch synthase II in the plant cell or plant.

Preferably, the foreign nucleic acid molecule is a recombinant nucleic acid molecule which consists of various components the combination or specific spatial disposition whereof does not occur naturally in plant cells.

In connection with the present invention, the term "recombinant nucleic acid molecule" should be understood to mean a nucleic acid molecule which possesses different nucleic acid molecules which are not present naturally in a combination in the way in which they are present in a recombinant nucleic acid molecule. Thus for example, as well as nucleic acid molecules which code for a protein with the activity of a starch synthase II (e.g. genomic nucleic acid molecules or cDNAs), the recombinant nucleic acid molecules have additional nucleic acid sequences which are not naturally present in combination with these nucleic acid molecules. For example, the recombinant nucleic acid molecule has control sequences (e.g. promoters, termination signals, enhancers), preferably control sequences which are heterologous with regard to the nucleic acid molecule which codes for the starch synthase II. In this connection, heterologous means that the control sequence is not the typical endogenous control sequence of the starch synthase II gene used. Also preferred are control sequences which are active in plant tissue.

Suitable promoters are constitutive promoters, such as for example the promoter of the 35S RNA of the cauliflower mosaic virus (Odell et al., 1985, Nature, 313, 810-812), the ubiquitin promoter from maize (Christensen et al., Plant Mol. Biol. 18, (1992), 675-689), the ubiquitin promoter from rice (Liu et al., Plant Science 165, (2003), the rice actin promoter (Zhang, et al., Plant Cell 3:1150-1160, 1991), the cassava vein mosaic virus (CVMV) promoter (Verdaguer et. al., Plant Mol. Biol. 31: 1129-1139), the maize histone H3C4 promoter (U.S. Pat. No. 6,750,378) or the *Cestrum* YLCV promoter (yellow leaf curling virus; WO 01 73087; Stavolone et al., 2003, Plant Mol. Biol. 53, 703-713).

Particularly preferably, they are tissue-specific control sequences which are active in wheat tissue, preferably in the endosperm of wheat plants. Further endosperm-specific promoters are the promoter of the 10 kD zein gene from maize (Kirihara et al. (1988) Gene 71: 359-370), the 15 kD zein gene from maize (Hoffmann et al. (1987) EMBO J. 6: 3213-3221; Schernthaner et al. (1988) EMBO J. 7: 1249-1253; Williamson et al. (1988) Plant Physiol. 88: 1002-1007), the 27 kd zein gene from maize (Prat et al. (1987) Gene 52: 51-49; Gallardo et al. (1988) Plant Sci. 54: 211-281), and the 19 kD zein gene from maize (Marks et al. (1985) J. Biol. Chem. 260: 16451-16459). The relative transcriptional activities of these promoters in maize are described in Kodrzyck et al., (1989), Plant Cell 1, 105-114).

Other promoters possible in connection with the present invention are the promoter of the sucrose synthase gene (Yang, N.-S. and Russel, D. (1990) Proc. Natl. Acad Sci 87: 4144-4148), the waxy gene (Unger et al. (1991) Plant Physiol. 96: 124), the sh 2 gene (Bhave et al. (1990) Plant Cell 2: 581-588, and the bt 2 gene (Bae et al. (1990) Maydica 35: 317-322). Also, the HMG promoter (also described as wheat glutenin HMWG promoter) from wheat (Colot et al., EMBO J. 6, (1987, 3559-3564; Clarke and Appels, Genome 41, (1998), 865-871), the USP promoter, the phaseolin promoter, promoters of zein genes from maize (Pedersen et al., Cell 29 (1982), 1015-1026; Quatroccio et al., Plant Mol. Biol. 15 (1990), 81-93), the glutelin promoter (Leisy et al., Plant Mol. Biol. 14 (1990), 41-50; Zheng et al., Plant J. 4 (1993), 357-366; Yoshihara et al., FEBS Lett. 383 (1996), 213-218), the globulin promoter (Nakase et al., 1996, Gene 170(2), 223-226) or the prolamine promoter (Qu and Takaiwa, 2004, Plant Biotechnology Journal 2(2), 113-125).

Preferably promoters which are specific for starch-storing organs are used, such as for example endosperm-specific promoters, such as for example the glutelin promoter (Leisy et al., Plant Mol. Biol. 14, (1990), 41-50; Zheng et al., Plant J. 4, (1993), 357-366; Yoshihara et al., FEBS Lett. 383, (1996), 213-218), the HMW promoter from wheat (Anderson, Theoretical and Applied Genetics 96, (1998), 568-576, Thomas, Plant Cell 2 (12), (1990), 1171-1180), the USP promoter, the phaseolin promoter (Sengupta-Gopalan, Proc. Natl. Acad. Sci. USA 82 (1985), 3320-3324, Bustos, Plant Cell 1 (9) (1989), 839-853) or the caryopse-specific promoters of GBSSI (granule bound starch synthase I) (DE10041861.9) and of SSII (soluble starch synthase II) from wheat (DE10032379.0).

Intron sequences can also be present between the promoter and the coding region. Such intron sequences can lead to stability of expression and to increased expression in plants (Callis et al., 1987, Genes Devel. 1, 1183-1200; Luehrsen, and Walbot, 1991, Mol. Gen. Genet. 225, 81-93; Rethmeier, et al., 1997; Plant Journal. 12(4):895-899; Rose and Beliakoff, 2000, Plant Physiol. 122 (2), 535-542; Vasil et al., 1989, Plant Physiol. 91, 1575-1579; XU et al., 2003, Science in China Series C Vol. 46 No. 6, 561-569). Suitable intron sequences are for example the first intron of the sh1 gene from maize (Maas et al. (1991) Plant. Mol. Biol. 16: 199-207, the first intron of the poly-ubiquitin gene 1 from maize, the first intron of the EPSPS gene from rice or one of the two first introns of the PAT1 gene from *Arabidopsis*, also introns of the Adh-1 or Bz-1 gene from maize (Callis et al. (1987) Genes Dev. 1: 1183-1200), the intron 3 of the maize actin gene (Luehrsen, K. R. and Walbot, V. (1991) Mol. Gen. Genet. 225: 81-93) or the Adh1 intron 6 (Oard et al. (1989) Plant Cell Rep 8: 156-160).

Methods for the creation of recombinant nucleic acid molecules are known to the person skilled in the art and comprise genetic engineering methods, such as for example the linking of nucleic acid molecules by ligation, gene recombination or the ab initio synthesis of nucleic acid molecules (see e.g. Sambrook et al., Molecular Cloning, A Laboratory Manual, 3rd edition (2001) Cold Spring Harbor Laboratory Press, Cold Spring Harbor, N.Y. ISBN: 0879695773, Ausubel et al., Short Protocols in Molecular Biology, John Wiley & Sons; 5th edition (2002), ISBN: 0471250929).

In connection with the present invention, the term "genome" should be understood to mean the totality of the genetic material present in a plant cell. It is well known to the person skilled in the art that as well as the cell nucleus, other compartments (e.g. plastids, mitochondria) contain genetic material.

Also a subject of the invention are genetically modified wheat plants which contain the wheat plant cells according to the invention. Such wheat plants can be created by regeneration from plant cells according to the invention.

The present invention also relates to propagative material of wheat plants according to the invention. Here, the term "propagative material" comprises those components of the plant which are suitable for the generation of progeny by the vegetative or sexual route. For vegetative propagation, callus cultures are for example suitable. Particularly preferably, the propagative material is endosperm-containing wheat seeds (grains).

Furthermore, the present invention also relates to a method for the production of a wheat plant according to the invention, wherein a) a wheat plant cell is genetically modified, whereby the genetic modification leads to an increase in the activity of a starch synthase II compared to corresponding non genetically-modified wild type wheat plant cells;
b) a wheat plant is regenerated from wheat plant cells from step a); and
c) optionally further wheat plants are created by means of the wheat plants according to step b).

For the genetic modification introduced into the wheat plant cell according to step a), the same applies as was already explained in connection with the description of the wheat plants (cells) according to the invention.

The regeneration of the wheat plants according to step b) can be effected by methods known to the person skilled in the art (e.g. described in "Plant Cell Culture Protocols", 1999, ed. by R. D. Hall, Humana Press, ISBN 0-89603-549-2).

The creation of further plants according to step c) of the method according to the invention can for example be effected by vegetative propagation (for example via callus cultures) or by sexual propagation. Here, the sexual propagation is preferably controlled, i.e. selected wheat plants with defined properties are crossed with one another and propagated. Here the selection is preferably made such that the wheat plants which are obtained according to step c) have the genetic modification which was introduced in step a).

In a further embodiment, the present invention relates to wheat flour containing the—preferably granular—wheat starch according to the invention.

Starch-storing parts of plants can be processed into flours. For the production of wheat flours, the endosperm-containing wheat grains are ground and sieved. Starch is a main component of the endosperm. The wheat starch according to the invention together with proteins and lipids is the main component of the wheat flour according to the invention. The properties of the wheat flours according to the invention are therefore strongly influenced by the wheat starch according to the invention contained in the wheat flour.

In connection with the present invention, the term "wheat flour" should be understood to mean a powder obtained by grinding of wheat grains, where the wheat grains consist of wheat plant cells which express a heterologous starch synthase II. Optionally, the wheat grains are dried before grinding and pulverized and/or sieved after the grinding.

In a further embodiment, the present invention relates to wheat flour the starch component whereof has an amylose content between 15.0 wt. % and 30.0 wt. %, preferably between 18.0 wt. % and 30.0 wt. % and particularly preferably between 20.0 wt. % and 30.0 wt. % and the wheat flour has a content of resistant starch of the flour (RS flour) of more than 5.0 wt. %, preferably between 5.0 wt. % and 30.0 wt. %, particularly preferably between 6.0 wt. % and 20 wt. %.

In connection with the present invention, the amylose content of the starch component of the wheat flour according to the invention is determined by means of the DSC method "determination of the content of apparent amylose" described later. As desired, the DSC method can be performed here on a wheat starch sample (a method for the isolation of wheat starch from wheat flour is described later under "Preparation of wheat flour and subsequent extraction of wheat starch") or on a wheat flour sample.

Preferably the DSC method is performed on a wheat flour sample. The amylose content of the starch is then obtained assuming an x % content by weight of the starch in a wheat flour sample (Hung et al., Trends in Food Science & Technology 17, (2006), 448-456) by calculation according to the following formula:

$$\text{Amylose content of the starch} = \frac{\text{amylose content (flour)} \times 100}{x}$$

The content by weight X of the starch in the flour sample is preferably determined as described in Method 8 (determination of the content of rapidly digestible and resistant starch in wheat flours/starches).

In connection with the present invention, the determination of the RS content of the wheat flour according to the invention (RS flour) is preferably performed by the method of Englyst et al. already mentioned above (Europ. J. of Clinical Nutrition 46 (Suppl. 2), (1992), pp 33-50, see in particular the following paragraphs from Englyst et al., page S35-S36: "Reagents, Apparatus, Spectrophotometer"; page S36-S37, Section "Measurement of free glucose (FG)"; and page S38, Section "Measurement of RDS and SDS"). In connection with the present invention, the percentage of the weighed out flour sample (fresh weight), which is not released as glucose after 2 hours in the method of Englyst et al. is described as the "RS content of the wheat flour". It is thus obtained according to the following formula:

RS flour in %=total glucose in % fresh weight−glucose released after 2 hrs as % fresh weight In a further preferred embodiment of the present invention, the statement of the amylose content is based not on the starch component of the wheat flour, but on the amylose content of the wheat flour according to the invention (amylose content flour). The amylose content of the wheat flours according to the invention (amylose content flour) is between 10.0 wt. % and 22 wt. %, preferably between 11 wt. % and 21 wt. % and particularly preferably between 12 wt. % and 20.0 wt. %.

In connection with the present invention, the amylose content of the wheat flour according to the invention (amylose content flour) is determined on a wheat flour sample by means of the DSC method described later "Determination of the content of apparent amylose".

In a further embodiment, the wheat flours according to the invention have a content of rapidly digestible flour (RDS flour) based on the quantity of flour (fresh weight) between 10 wt. % and 22 wt. %, preferably between 11 wt. % and 21 wt. %, particularly preferably between 12 wt. % and 20 wt. %.

In connection with the present invention, "the content of rapidly digestible flour (=RDS flour)" should be understood to mean the percentage of a wheat flour which in the aforesaid method of Englyst et al. for the determination of the RS content is released as glucose after 20 minutes. Here, the statement in weight percent is based on the fresh weight of the flour sample. Thus the following applies in connection with the present invention:

RDS flour in %=released glucose after 20 minutes in % fresh weight

In a further embodiment, the present invention relates to wheat flour, the starch component whereof has an amylose content between 15.0 wt. % and 30.0 wt. %, preferably between 18.0 wt. % and 29.5 wt. % and particularly preferably between 20.0 wt. % and 29.5 wt. % and the wheat flour has a) a content of resistant starch of the flour (RS flour) of more than 5.0 wt. %, preferably between 6.0 wt. % and 30.0 wt. %; and b) a content of rapidly digestible flour (RDS flour) based on the quantity of flour (dry weight) between 10 wt. % and 22 wt. %, preferably between 11 wt. % and 21 wt. %, particularly preferably between 12 wt. % and 20 wt. %.

In a further embodiment, the present invention relates to wheat flour the starch component whereof has an amylose content between 15.0 wt. % and 30.0 wt. %, preferably between 18.0 wt. % and 30.0 wt. % and particularly preferably between 20.0 wt. % and 30.0 wt. % and the starch component whereof has a content of resistant starch (RS starch) of more than 5.0 wt. %, preferably between 6 wt. % and 30.0 wt. %.

In connection with the present invention, the determination of the RS content of the starch component (RS starch) of the wheat flour according to the invention is effected as described above for the wheat starch according to the invention.

In a further embodiment, the starch component of the wheat flour according to the invention has a content of rapidly digestible starch (RDS starch) between 10.0 wt. % and 38 wt. %, preferably between 15.0 wt. % and 35.0 wt. %, particularly preferably between 20.0 wt. % and 33 wt. %.

In connection with the present invention, the determination of the RDS content of the starch component (RDS starch) of the wheat flour according to the invention is effected as described above for the wheat starch according to the invention.

The wheat starches/wheat flours according to the invention have the advantage of a decreased content of rapidly digestible flour/starch which is particularly advantageous since a rapid release of larger quantities of glucose and its absorption via the small intestine epithelium leads to an abrupt increase in the blood sugar level.

As a result of this, there is an outpouring of insulin (insulin response). The continual consumption of foodstuffs with a high glycemic loading, and the insulin outpouring associated therewith, is suspected to be a risk factor in the onset of diseases such as hypertension, overweight, heart disease and type II diabetes.

In a further embodiment, the present invention relates to wheat flour, the starch component whereof has an amylose content between 15.0 wt. % and 30.0 wt. %, preferably between 18.0 wt. % and 29.5 wt. % and particularly preferably between 20.0 wt. % and 29.5 wt. % and the starch component whereof has a) a content of resistant starch (RS starch) of more than 5.0 wt. %, preferably between 6.0 wt. % and 30.0 wt. %; and b) a content of rapidly digestible starch (RDS starch) between 10.0 wt. % and 38 wt. %, preferably between 15.0 wt. % and 35.0 wt. %, particularly preferably between 20.0 wt. % and 33 wt. %.

In a further embodiment, the present invention also relates to wheat flours, the starch component whereof has an amylose content between 15.0 wt. % and 30.0 wt. %, preferably between 18.0 wt. % and 30.0 wt. % and particularly preferably between 20.0 wt. % and 30.0 wt. % based on the starch, and the flour has a DSC T-onset temperature between 63.0° C. and 70.0° C., preferably between 64.0° C. and 69.0° C., particularly preferably between 65.0° C. and 68.0° C.

In a further embodiment, the wheat flours according to the invention exhibit an increase in the DSC T-onset temperature by 2° C. and 9° C., preferably by 3° C. and 7° C., compared to the DSC T-onset temperature of corresponding wheat flours from wild type wheat plants.

In a further embodiment, the wheat flour according to the invention has a DSC T-peak temperature between 70.0° C. and 78.0° C., preferably between 71.0° C. and 75.0° C.

In a further embodiment, the wheat flours according to the invention exhibit an increase in the DSC T-peak temperature by 2° C. and 8° C., preferably by 3° C. and 7° C., compared to the DSC T-peak temperature of corresponding wheat flours from wild type wheat plants.

It was surprising to the person skilled in the art that the DSC-T-onset and DSC T-peak temperature of the wheat starch or flours according to the invention was markedly increased compared to corresponding starches or flours from wild type wheat plants. In particular because an increase in the thermal stability is normally to be observed in starches/flours with increased amylose content compared to wild type starches/flours, however the wheat starches and flours according to the invention exhibit an amylose content which is not increased compared to starches/flours from wild type wheat plants.

In many thermal processes and applications, the use of (granular) wheat starches or of wheat flours containing such (granular) wheat starches is desirable. The high DSC T-onset or T-peak temperature of the wheat starch according to the invention or of the wheat flour according to the invention is therefore especially advantageous, since the maintenance of the structure of the starch granules is ensured because of this property even at elevated process temperatures.

The wheat flours according to the invention are distinguished by markedly improved processability compared to previously known wheat flours with increased RS content or decreased content of RDS, which in these is attributable to a markedly increased amylose content compared to wild type wheat flours.

The wheat starches described in the state of the art with an amylose content of >70 wt. % (Regina et al., PNAS 103 (10), (2006), 3546-3551) have the disadvantage of poor processing properties, since these starches hardly pregelatinize, have an increased tendency to retrogradation and low swelling capacity, and are poorly soluble in water. For applications in which only pregelatinized starches are usable or the tendency to retrogradation should be decreased (e.g. for avoidance of ageing processes in bakery products) or a higher swelling capacity or higher solubility are necessary, these wheat starches with an amylose content of >70 wt. % are thus either absolutely unsuitable or they must be additionally chemically modified in order to introduce the desired properties. Compared to these wheat starches and flours with an amylose content >70 wt. %, the wheat starches and flours according to the invention have the advantage that advantageous digestive properties (increased RS content, decreased content of RDS) are paired with advantageous processing properties (e.g. thermal stability, swelling capacity, solubility, pregelatinization). As a result, the wheat starches and flours according to the invention are more suitable for applications wherein either only pregelatinized starches are usable and/or wherein a higher swelling capacity and/or higher solubility and/or increased thermal stability are necessary.

In particular, compared to the wheat flours with increased RS content described in the state of the art, the wheat flours according to the invention have the advantage of increased dough stability of the doughs which can be produced from the wheat flour according to the invention, since the dough which is produced from the wheat flour of an SSIIa-inhibited wheat plant exhibits increased dough stability (Morita et al., Cereal Chemistry 79, (2002), 491-495; Hung et al., Cereal Chemistry 82, (2005), 690-694; Hung et al., Trends in Food Science & Technology 17, (2006), 448-456). Further, compared to the wheat flour of SSIIa-inhibited wheat plants, the wheat flours according to the invention have the advantage that on baking they do not exhibit the undesired decrease in bread volume (Morita et al., Cereal Chemistry 79, (2002), 491-495). Furthermore, compared to high amylose wheat flours, the wheat flours according to the invention have the advantage that owing to their good processing properties they can be used alone, whereas high amylose content wheat flours owing to their poor processing quality can only be used in mixtures with conventional wheat flours (Hung et al., Trends in Food Science & Technology 17, (2006), 448-456). Hence, through the present invention for the first time wheat flours with increased RS content and/or decreased RDS content compared to wheat flour from wild type wheat plants are provided, which furthermore have considerably improved processing properties compared to high amylose content RS wheat flours from wheat plants with inhibited gene expression of the SSIIa (Yamamori et al., Australian Journal of Agricultural Research 57, (2006), 531-53) or the branching enzyme BEIIa (Regina et al., PNAS Vol. 103 No. 10, (2006), 3546-3551).

In a further embodiment, the present invention relates to a wheat flour the starch component whereof has an amylose content between 15.0 wt. % and 30.0 wt. %, preferably between 18.0 wt. % and 29.5 wt. % and particularly preferably between 20.0 wt. % and 29.5 wt. % and in addition the flour optionally has a) a content of resistant starch of the flour (RS flour) of more than 5.0 wt. %, preferably between 6.0 wt. % and 30.0 wt. %; and/or b) a content of rapidly digestible flour (RDS flour) based on the quantity of flour (dry weight) between 10 wt. % and 22 wt. %, preferably between 11 wt. % and 21 wt. %, particularly preferably between 12 wt. % and 20 wt. %; and/or c) a DSC T-onset temperature between 63.0° C. and 70.0° C., preferably between 64.0° C. and 69.0° C., particularly preferably between 65.0° C. and 68.0° C.; and/or d) DSC T-peak temperature between 70.0° C. and 78.0° C., preferably between 71.0° C. and 75.0° C.

A further subject of the present invention is a method for the production of the wheat flours according to the invention comprising the step of grinding at least one wheat plant which expresses a heterologous starch synthase II.

In a further embodiment of the method according to the invention for the production of the flours according to the invention, wheat grains which consist of wheat plant cells (according to the invention) which express a heterologous starch synthase II are ground.

Preferably the method according to the invention for the production of wheat flours also includes the step of harvesting the wheat plants (according to the invention) or the wheat grains of these wheat plants before grinding, preferably the washing of the wheat plants (according to the invention) or the wheat grains before grinding and further the step of the cultivation of the wheat plants (according to the invention) before the harvesting.

In a further embodiment of the present invention, the method according to the invention for the production of flours includes a processing of the wheat plants (according to the invention) or wheat grains the plant cells whereof express a heterologous starch synthase II, before grinding.

The processing here can for example be a heat treatment and/or drying. The pulverization of wheat plants, of starch-storing parts or wheat grains of such wheat plants (according to the invention) before grinding can also represent a processing in the sense of the present invention. The removal of plant tissue, such as for example the husks of the grains, before grinding also represents a processing before grinding in the sense of the present invention.

In a further embodiment of the present invention, the method for the production of flours after the grinding includes a processing of the grist. Here for example the grist can be sieved after the grinding, in order for example to produce various type flours.

In a further embodiment, the present invention relates to the use of wheat flour according to the invention for the production of a foodstuff.

In a further embodiment the present invention relates to the use of wheat flour according to the invention as a prebiotic.

In a further embodiment, the present invention relates to a composition containing the wheat starch according to the invention and at least one food additive.

In a further embodiment the present invention relates to a composition containing the wheat flour according to the invention and at least one food additive.

As food additives in connection with the present invention for example vitamins (e.g. vitamin A, B1, B2, B3, B5, B6, B9, B12, C, D, E, F, K), provitamins, antioxidants, trace elements (e.g. chromium, iron, fluorine, iodine, cobalt, copper, manganese, molybdenum, selenium, vanadium, zinc), minerals (e.g. calcium, chlorine, potassium, magnesium, phosphorus, sulfur, sodium), flavorings, colorants, oils, fats, fatty acids, in particular (multiply) unsaturated fatty acids, essential fatty acids, carbohydrates (e.g. starches, galactooligosaccharides, gentiobiose, tagatose), roughage (e.g. cellulose, hemicellulose, pectin, lignin), prebiotics (e.g. oligofructose, oligosaccharides, chitosan, beta glucans, arabinogalactan), probiotics (e.g. bifidobacteria, lactic acid bacteria such as for example the genus *Lactobacillus*), i.e. non-pathogenic microorganisms which are added live or in spore form to the foodstuff and can favorably influence the intestinal flora, may be mentioned.

The production of the compositions according to the invention can for example be effected by simple mixing.

In a further embodiment, the present invention relates to a foodstuff containing the wheat starch according to the invention.

In a further embodiment, the present invention relates to a foodstuff containing the wheat flour according to the invention.

In a further embodiment, the present invention relates to a foodstuff containing the composition according to the invention.

Typical foodstuffs which can be produced using the wheat starch according to the invention, the wheat flour according to the invention or the composition according to the invention are for example tortillas, tortilla crisps, bakery products (e.g. bread, wheat bread, rolls, cookies, cakes, waffles, muffins, unleavened wheat cakes, bagels), pancakes, pizzas, pasta (e.g. noodles), stews, sauces, wheat flour pudding, dairy products (e.g. yoghurt, curd cheese, ice-cream), puddings, spreads (e.g. butter, margarine), drinks, powdered drinks, ready-to-serve meals, (breakfast) cereals, sausages, meat products, baby food, ketchup, mayonnaise, barbecue sauces and the like.

Material and Methods

In the examples, the following methods were used. These methods can be used for the implementation of the methods according to the invention, they are concrete embodiments of the present invention, but the do not limit the present invention to these methods.

1) Plant Material and Cultivation

Wheat Plants: *Triticum aestivum*, Variety *Fielder*

The cultivation of the wheat plants in the greenhouse was carried out under the following conditions:

Substrate: special mixture for sowing

80% white peat

20% black peat 100 kg/m$^3$ sand 40 kg/m$^3$ moist clay structure: fine pH value: 5.3-6.1

Basic manuring: 2 kg/m$^3$ 12-12-17 (+2) and 100 g/m$^3$ Radigen (Theraflor GmbH; Iserlohn; Germany)

Pots: 12 cm square pot

Spacing: max. 64 plants/m$^2$

Manuring: Leaf manuring with 1% Vitanica Si (5-3-7)+ 10% silicate (Compo Co.)

Hakaphos blau (15-10-15+2) 0.2 g/plant

Temperature: day 22-25° C./night 16° C.

Light: 16 hours, 350-400 µEinstein/s/m

Atm. humidity: 50% rel.

Plant protection measures: as needed (insecticide e.g.: Karate Zeon, fungicide e.g. Stratego)

2) Origin of the Sequences and Constructs Used for the Transformation

For the transformation of wheat a mutagenized form of the OsSSII-3 from rice was used. Isolation and cloning were effected as described in Example 1. The transformation vector pBA71 used is described in Example 1.

3) Transformation and Regeneration of Wheat Plants

Wheat plants were transformed and regenerated according to the method described by Wu et al. (2003; Wu H, Sparks C, Amoah B, Jones H D (2003) Factors influencing successful *Agrobacterium*-mediated genetic transformation of wheat. Plant Cell Reports 21:659-6686).

4) Production of T1 Grains

For the production of T1 grains, after reaching a sufficient plant size the plants regenerated in tissue culture were transferred into pots containing soil. The cultivation and the composition of the soil are described under 1). The plants were at first covered with a plastic hood in order to avoid excessive moisture loss. The flowers were fertilized by self-pollination. The grains were left on the plant until ripe and after harvesting were dried for 3-5 days at 37° C.

5) Production of T2 Grains with the Use of Embryo Rescue

In order to effect the timely production of T2 grains, T1 grains were harvested before the onset of dormancy and freed from the covering husks. For the sterilization of the seed surface, the seeds were incubated in an Eppendorf vessel for one minute with 70% ethanol, before the ethanol was replaced by a 1% sodium hypochlorite (NaOCl) solution, in which the seeds remained for 20 minutes. For complete removal of the NaOCl, the seeds were washed three times in succession with water. The embryos were separated from the endosperm under sterile conditions and placed on Petri dishes with MS medium (Murashige and Skoog (1962); Physiol. Plant. 15:473-497) containing 3% saccharose for germination. After incubation for 3 days in the dark, the Petri dishes with the embryos were brought into the light. The germinated plants were transferred into jars with MS medium containing 2% saccharose and left there until attainment of a size sufficient for transfer into soil culture. The further production of T2 grains was effected by the procedure described under 4).

6) Production of Wheat Flours and Subsequent Extraction of Wheat Starch

For analyses on a small scale, wheat grains were filled into 2 ml Eppendorf vessels and pulverized together with a tungsten carbide ball for 30 seconds at 30 Hertz in a ball mill from the company Retsch GmbH (Haan). The resulting flour was used as the starting material for all further analyses.

For the production of larger quantities of flour as a starting material for the extraction of wheat starch, wheat grains were milled to a type flour 550 in a Brabender mill (Type Quadrumat Junior; Brabender GmbH, Duisburg). In each case, 10 g of wheat flour (type 550) were filled into the Glutomatic gluten wash machine (Perten GmbH; Hamburg) and the machine operated according to the manufacturer's instructions. The starch is collected as an aqueous suspension and then sedimented by centrifugation (3000 rpm, 10 min, RT). The pellet is again resuspended in water and the resulting suspension centrifuged as described above. The upper yellowish/brown layer of the sediment was removed manually and the remaining sediment resuspended in acetone. After renewed centrifugation, the supernatant was discarded and the starch pellet dried under the fume hood.

Before further use, the starch was processed to a fine powder using mortars.

7) Thermal Analysis of Wheat Flour by Heat Flow Calorimetry Method (Differential Scanning Calorimetry (DSC))

In each case, 10 mg of wheat flour or wheat starch were treated with 30 µl of doubly distilled water in a stainless steel pan (Perkin Elmer, "Large Volume Stainless Steel Pans" [03190218], volume 60 µl) and this was then hermetically sealed. The sample was heated from 20° C. to 150° C. in a Diamond DSC instrument (Perkin Elmer) at a heating rate of 10° C./min. At the same time, an empty sealed stainless steel pan is used as the reference. The system was calibrated with defined quantities of indium. The data analysis was performed using a software program from Pyris (Perkin Elmer, Version 7.0). The further processing of assessable raw data was performed by analysis of the individual peaks of the 1$^{st}$ order phase transitions for the T-onset (° C.), T-peak (° C.), T-end (° C.) and dH (J/g) (the standard here is the straight baseline). DSC T-onset here is characterized as the intersection point between the extension of the base line and the tangent laid on the rising flank of the peak through the inflexion point. It characterizes the start of the phase transformation.

The maximum temperature at which the DSC curve has reached a maximum (i.e. that temperature at which the first derivative of the curve is zero) is described as the maximum temperature DSC T-peak.

In the function used in Pyris (calc-peak Area), a start and end temperature for the baseline fit are inputted manually.

8) Determination of the Content of Rapidly Digestible and Resistant Starch in Wheat Flours/Starches The determination of the content of resistant starch is effected on the basis of the method described after Englyst et al. (Europ. J. of Clinical Nutrition 46 (Suppl. 2), (1992), S 33-50)) (see in particular the following sections from Englyst et al., page S35-S36: "Reagents, Apparatus, Spectrophotometer"; page S36-S37, Section "Measurement of free glucose (FG)"; page S38, and Section "Measurement of RDS and SDS").

For the production of the enzyme solution 1.2 g of pancreatin (Merck) are extracted in 8 ml of water for 10 minutes at 37° C. After centrifugation (10', 3000 rpm; RT), 7.02 ml of the supernatant are treated with 1.227 ml of demineralized water and 0.136 ml of amyloglucosidase (3260 U/ml) (Sigma-Aldrich, Taufkirchen).

In parallel, 10 mg (dry weight) of wheat flour or starch per sample in a 2 ml reaction vessel are treated with 0.75 ml of sodium acetate buffer (0.1 M sodium acetate pH 5.2; 4 mM $CaCl_2$) and incubated for 5 minutes at 37° C. to warm the preparation.

In each case, the digestion of the starch is started by addition of 0.25 ml of enzyme solution per preparation. A preparation with no starch is used as control. After 20 and 120 minutes, aliquots of 50 μl are withdrawn and placed on ice for 10 mins each with 12.5 μl of 25% TCA, whereby the enzymes are inactivated. After centrifugation (2', 13 000 rpm; RT), 25 μl of the supernatant are diluted to 1 ml with water.

For the determination of the total starch, after the 120 min sampling, 150 μl of heat-stable α-amylase (53 U) in MOPS buffer (50 mM; pH 7.0) are added to each of the preparations. Next, the samples are shaken for 6 mins at 95° C. Then the samples are cooled at RT for 5 mins, before 200 μl of amyloglucosidase (4.5 U) in NaOAc buffer (200 mM, pH 4.5) are added to each. After 60 mins incubation at 50° C., aliquots of 50 μl are withdrawn and inactivated and diluted as above.

The diluted samples are used for the measurement of the content of released glucose after 20 min, 120 min and after total starch solubilization. For this, 20 μl of diluted sample are mixed with 180 μl of assay buffer (100 mM imidazole/HCl pH 6.9; 5 mM $MgCl_2$; 1 mM ATP; 2 mM NADP) and the absorption of the sample at 340 nm determined. The reaction of the glucose is started by addition of 2 μl of enzyme mix (10 μl hexokinase, 10 μl glucose-6-phosphate dehydrogenase, 80 μl assay buffer) and the equimolar conversion of NADP to NADPH followed at 340 nm until attainment of a plateau. The quantities of glucose determined are compared to the quantity weighed out and give the proportion of the sample which was released as glucose after the corresponding time period. In particular, with wheat flours the values for released glucose after 20 mins and 120 mins can also be compared to the quantity of total glucose, since the content of starch in the fresh weight can vary.

9) Preparation of Wheat Flour/Starch for Study of the Amylopectin Side-Chain Distribution by High Pressure Anion Exchange Chromatography 10 mg per sample of wheat flour or starch were weighed into a 2 ml Eppendorf cup and treated with 250 μl of 90% (v/v) DMSO. After 1 hour dissolution of the sample with shaking at 95° C., 375 μl of water were added and the preparation incubated for one hour at 95° C. 300 μl of 16.7 mM sodium acetate pH 3.5 and 0.5 U of isoamylase from *Pseudomonas* sp. (Megazyme; Bray, Ireland) were added to 200 μl of the preparation and incubated for 24 hours at 37° C.

For the chromatography, 50 μl of the preparation were diluted 1:10 with water and then filtered through 0.22 μm nylon filters. About 50 μl of the filtrate were injected.

Chromatography Method:

HPLC system: GP 50 Dionex Gradient Pump

ED 50 Dionex Electrochem. Detector/PAD

AS 50 Autosampler

Column oven

Column: Dionex CarboPac PA 100 4×250 mm (P/N 046110)

with Guard Column PA 100 4×50 mm (P/N 046115)

Instrument Configuration:

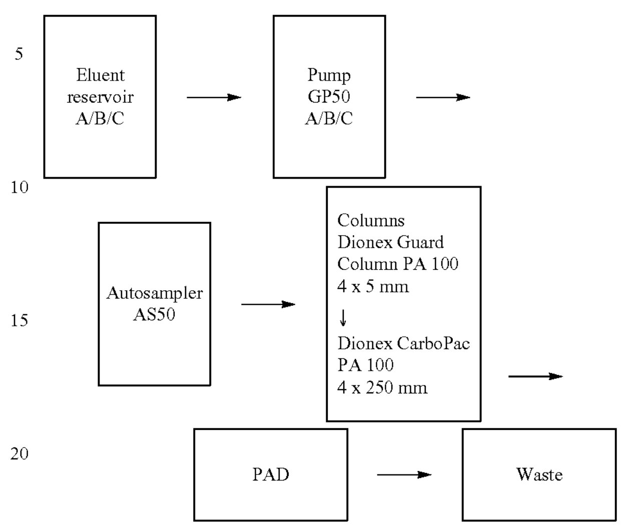

HPAEC Program:

| | | |
|---|---|---|
| | Pressure.LowerLimit = | 50 |
| | Pressure.UpperLimit = | 3500 |
| | %A.Equate = | "Water" |
| | %B.Equate = | "NaOAc 1.0 M in NaOH 0.25 M" |
| | %C.Equate = | "NaOH 0.25 M" |
| | ECD.Data_Collection_Rate = | 1.0 |
| | Waveform Time = 0.00, Potential = | 0.05 |
| | Waveform Time = 0.20, Potential = | 0.05, Integration = Start |
| | Waveform Time = 0.40, Potential = | 0.05, Integration = End |
| | Waveform Time = 0.41, Potential = | 0.75 |
| | Waveform Time = 0.60, Potential = | 0.75 |
| | Waveform Time = 0.61, Potential = | −0.15 |
| | Waveform Time = 1.00, Potential = | −0.15 |
| | Cell = | On |
| | Pump_Pressure.Formula | Formula=Pump.Pressure |
| | Pump_Pressure.Type = | Analog |
| | Pump_Pressure.Step = | Auto |
| | Pump_Pressure.Average = | On |
| | Flush | Volume = 500 |
| | Wait | FlushState |
| | NeedleHeight = | 2 |
| | CutSegmentVolume = | 1 |
| | SyringeSpeed = | 4 |
| | Cycle = | 0 |
| | WaitForTemperature = | False |
| | Wait | SampleReady |
| 0.000 | Flow = | 1.00 |
| | %B = | 0.0 |
| | %C = | 100.0 |
| | %D = | 0.0 |
| | Curve = | 5 |
| | Load | |
| | Inject | |
| | Wait | InjectState |
| | ECD.Autozero | |
| | ECD_1.AcqOn | |
| | Pump_Pressure.AcqOn | |
| | Flow = | 1.00 |
| | %B = | 0.0 |
| | %C = | 100.0 |
| | %D = | 0.0 |
| | Curve = | 5 |
| 4.000 | Flow = | 1.00 |
| | %B = | 11.0 |
| | %C = | 89.0 |
| | %D = | 0.0 |
| | Curve = | 5 |

-continued

| | | |
|---|---|---|
| | Flow = | 1.00 |
| | %B = | 11.0 |
| | %C = | 89.0 |
| | %D = | 0.0 |
| | Curve = | 4 |
| 95.000 | Flow = | 1.00 |
| | %B = | 35.0 |
| | %C = | 65.0 |
| | %D = | 0.0 |
| | Curve = | 4 |
| 97.000 | Flow = | 1.00 |
| | %B = | 100.0 |
| | %C = | 0.0 |
| | %D = | 0.0 |
| | Curve = | 5 |
| 98.000 | Flow = | 1.00 |
| | %B = | 100.0 |
| | %C = | 0.0 |
| | %D = | 0.0 |
| | Curve = | 5 |
| 105.000 | Flow = | 1.00 |
| | %B = | 0.0 |
| | %C = | 100.0 |
| | %D = | 0.0 |
| | Curve = | 5 |
| 106.000 | Flow = | 1.00 |
| | %B = | 0.0 |
| | %C = | 5.0 |
| | %D = | 95.0 |
| | Curve = | 5 |
| 112.000 | Flow = | 1.00 |
| | %B = | 0.0 |
| | %C = | 5.0 |
| | %D = | 95.0 |
| | Curve = | 5 |
| ECD_1.AcqOff | | |
| Pump_Pressure.AcqOff | | |
| | End | |

The data assessment is effected with Dionex Chromeleon v6.70 (Dionex Corporation, Sunnyvale, Calif., USA). The manual "Tutorial and User Manual" for Version 6.60, March 2004, can be obtained via Dionex or downloaded via the homepage (world wide web at dionex.com).

For the comparison of the chromatograms, for each chromatogram the identified peaks of the different maltooligasaccharides were mean value-normalized (sum of all peak areas=1). The assessment was effected on the basis of the "force common baseline" as described in the Dionex Chromeleon v.6.60 regarding "log baseline". Here the log baseline is set shortly before the first side-chain peak and up to the last assessable peak of the shortest chromatogram of a measurement procedure, and the last assessable peak for all chromatograms is calculated from this.

10) Determination of the Content of Apparent Amylose by DSC

The amylose content of wheat flour/starch was determined by DSC on the basis of the method of Polaske et. Al (2005) (Starch 57:118-123).

The measurement principle of method is based firstly completely melting starch—consisting of amylose and amylopectin—in the presence of a lipid solution and then cooling again. In the course of the cooling process, the formation of amylose-lipid complexes occurs, the formation whereof leads to a release of energy which becomes visible as a peak in the thermogram and accordingly can be evaluated. Here, the peak area corresponding to the quantity of energy released is directly proportional to the quantity of amylose in the sample.

For the measurement, 10 mg of wheat flour/starch were weighed into a stainless steel pan (Perkin Elmer, "Large Volume Stainless Steel Pans" [03190218], volume 60 μl) and treated with 50 μl of a 2% aqueous L-α-lysophosphatidylcholine (LPC) solution. Next, the pans were hermetically sealed and firstly heated from 25° C. to 125° C. in the Diamond DSC device (Perkin-Elmer Inc, USA) at a heating rate of 10° C./min, left at this temperature for 2 minutes and then cooled from 125° C. to 60° C. at an identical cooling rate. Here, an empty sealed stainless steel pan was used as the reference. The system was calibrated with defined quantities of indium.

The data analysis was performed using a software program from Pyris (Perkin Elmer, Version 7.0). For the determination of the amylose content of a sample, the area of the peak (deltaH) in the cooling phase in the temperature range between 65° C. and 105° C. was determined and related to the quantity weighed out. For normalization of the system, parallel samples of known amylose content are analyzed and from this data a calibration curve which is used for the calculation of the amylose content (expressed in % FG) in the sample is drawn up.

11) Analysis of Wheat Starch with Rapid Visco Analyzer (RVA)

The principle of this analysis is based on subjecting suspension consisting of water and wheat starch a defined temperature and shear protocol and continuously recording the viscosity of the suspension during this. As the measuring instrument, an RVA Super3 from the company Newport Scientific (Macclesfield, UK) with the corresponding Software "Thermocline for Windows", Version 2.3 is used.

For the analysis, 2.5 g of wheat starch (quantity weighed out as pure dry weight of the sample material, corrected to 0% moisture) were weighed into a measurement vessel, treated with 25 ml of water, and the measuring instrument clamped into the instrument after insertion of a stirrer.

The following temperature and shear profile was applied: (corresponds to the "RVA method for wheat and rye flour" of Newport Scientific; Australia)

| Time | Type | Value |
|---|---|---|
| 00:00:00 | Temp | 50° C. |
| 00:00:00 | Speed | 960 rpm |
| 00:00:10 | Speed | 160 rpm |
| 00:01:00 | Temp | 50° C. |
| 00:04:42 | Temp | 95° C. |
| 00:07:12 | Temp | 95° C. |
| 00:11:00 | Temp | 50° C. |
| 00:13:00 | End of test | |

After completion of the measurement, the following parameters were determined:

Peak viscosity (highest viscosity between 2 and 7 minutes measurement time)

Trough viscosity (lowest viscosity between 7 and 12 minutes measurement time)

Final viscosity (viscosity at end of measurement)

Breakdown=peak−trough

Setback=final−trough

Pasting temperature (temperature, at which in a time interval of 0.5 minutes the viscosity changes by more than 50 cP)

Peak time (time at which the peak viscosity is reached)

12) Determination of the Phosphate Content at the C6 Position (C6-P Content)

In starch, the C3 and C6 positions of the glucose units can be phosphorylated. For the determination of the C6-P content of the starch, (modified after Nielsen et al., 1994, Plant Physiol. 105: 111-117) 50 mg of wheat flour/starch were hydrolyzed in 500 μl of 0.7 M HCl for 4 hrs at 95° C. with constant shaking. Next, the preparations were centrifuged for 10 mins at 15,500 g and the supernatants freed from suspended matter and turbidity by means of a filter membrane (0.45 μM). 20 μl of the clear hydrolyzate were mixed with 180 μl of imidazole buffer (300 mM imidazole, pH 7.4; 7.5 mM $MgCl_2$, 1 mM EDTA and 0.4 mM NADP). The measurement was performed in the photometer at 340 nm. After determination of the base absorption, the enzyme reaction was started by addition of 2 units of glucose-6-phosphate dehydrogenase (from *Leuconostoc mesenteroides*, Boehringer Mannheim). The change in absorption is due to equimolar conversion of glucose-6-phosphate and NADP to 6-phospho-gluconate and NADPH, the formation of the NADPH being determined at the aforesaid wavelength. The reaction was followed until attainment of a plateau. The result of this measurement yields the content of glucose-6-phosphate in the hydrolyzate. From the identical hydrolyzate, the degree of hydrolysis was determined on the basis of the content of released glucose. This is used in order to relate the content of glucose-6-phosphate to the content of hydrolyzed starch from the quantity fresh weight. For this, 10 μl of hydrolyzate were neutralized with 10 μl of 0.7 M NaOH and then diluted 1:100 with water. 4 μl of this dilution were treated with 196 μl of assay buffer (100 mM imidazole pH 6.9; 5 mM $MgCl_2$, 1 mM ATP, 0.4 mM NADP) and used for the determination of the base absorption. The reaction was started by addition of 2 μl of enzyme mix (hexokinase 1:10; glucose-6-phosphate dehydrogenase from yeast 1:10 in assay buffer) and followed at 340 nm until the plateau. The measurement principle is the same as that of the first reaction.

The result of this measurement yields the quantity of glucose (in mg) which was released from the starch present in the starting material in the course of the hydrolysis.

Then the result of both measurements is expressed as a ratio in order to express the content of glucose-6-phosphate per mg hydrolyzed starch. Through this calculation, in contrast to relating the quantity of glucose-6-phosphate to the fresh weight of the sample, the quantity of glucose-6-phosphate is related only to the part of the starch which was completely hydrolyzed to glucose and hence is also to be regarded as the source for the glucose-6-phosphate.

13) Determination of SSII Activity Using Activity Gel

The detection of the various starch synthase activities in unripe wheat grains was effected using activity gels (zymograms) for which protein extracts are separated under native conditions in a polyacrylamide gel and then incubated with appropriate substrates. The resulting reaction product (starch) was stained in the gel using Lugol's solution (2% (w/v) KI; 0.2% (w/v) $I_2$).

Individual unripe wheat grains (ca. 15 days after flowering—measured from day of start of flowering) were shock frozen in liquid nitrogen and homogenized in 150-200 μl of cold extraction buffer (50 mM Tris/HCl pH 7.6, 2.5 mM EDTA, 2 mM DTT, 4 mM PMSF, 0.1% (w/v) glycogen, 10% (v/v) glycerin). After centrifugation (15 mins, 13,000 g, 4° C.) the clear supernatant was transferred to a fresh reaction vessel and an aliquot of the extract was used for the determination of the protein content after Bradford (1976, Anal Biochem 72: 248-254).

The separation of the protein extracts was effected using a continuous 7.5% polyacrylamide gel (7.5% AA/BAA 37.5:1; 25 mM Tris/HCl pH 7.6, 192 mM glycine, 0.1% (w/v) APS, 0.05% (v/v) TEMED) with the use of 1× concentrated run buffer (25 mM Tris/HCl, 192 mM glycine). Before loading of the gels, a prerun to remove radicals is effected for 30 minutes at 8 mA and 4° C. For each sample, 30 μg of protein were applied and the electrophoresis performed for 2-2.5 hours at 4° C.

Next, the gels were incubated in 15 ml of incubation buffer (0.5M sodium citrate pH 7.0, 25 mM potassium acetate, 2 mM EDTA, 2 mM DTT, 0.1% (w/v) amylopectin, 50 mM Tricine/NaOH pH 8.5, 1 mM ADP-glucose) overnight at room temperature with constant shaking. The starch formed was stained with Lugol's solution.

In order to determine the factor by which the activity of a protein with the activity of a starch synthase II is increased compared to corresponding non genetically-modified wild type plants, protein extracts of the genetically modified lines were each sequentially diluted and separated electrophoretically according to the method described above. The further steps were effected as already described above. After staining of the zymograms with Lugol's solution, an optical comparison of the stained products produced by a protein with the activity of a starch synthase II was performed for the various dilutions of the protein extracts from genetically modified plants with the relevant products of the undiluted wild type protein extract. Since the intensity of the staining of the products correlates directly with the activity of a protein with the activity of a starch synthase II, bands of the products with equal intensities exhibit the same activity. If the band of the product of a protein with the activity of a starch synthase II in the diluted protein extract exhibits the same intensity as the relevant band of the product from corresponding undiluted protein extract from wild type plants, then the dilution factor corresponds to the degree of increase in the activity in the relevant genetically modified plant.

The following examples illustrate the invention described above.

EXAMPLE 1

Preparation of the Vector pBA71 for Expression of a Synthetic, Mutagenized Form of the Starch Synthase II-3 from Rice (=synthSS2 Os mut) in Wheat Functional Components of the Transformation Vector The vector pBA71 is a derivative of the plasmid pGREEN (Hellens et al., 2000). The "backbone" of the plasmid contains the following functional components:

[1] The "origin of replication" of the plasmid pBR322 (Bolivar et al., 1977) for replication in *Escherichia coli* (ORI ColE1)

[2] A selection marker mediating resistance to kanamycin (nptI; Grindley and Joyce, 1980) for propagation in *Escherichia coli* and *Agrobacterium tumefaciens*.

[3] The "origin of replication" of the plasmid pSA (Tait et al., 1982) for replication in *Agrobacterium* (ORI pSA)

The genetic components transferred into the plant genome are shown in the vector map (see FIG. 1) and described in detail in Table 1.

TABLE 1

Description of the genetic components which are inserted into the plant genome

| Nt Positions | Orientation | Origin |
|---|---|---|
| 540-563 | | LB: "left border repeat" of the T-DNA of *Agrobacterium tumefaciens* (Zambryski, 1988) |

TABLE 1-continued

| Description of the genetic components which are inserted into the plant genome | | |
|---|---|---|
| Nt Positions | Orientation | Origin |
| 615-2623 | Clockwise | PUbiZm + intron: promoter and intron of the ubiquitin-1 gene (ubi1) from *Zea mays* (Christensen et al., 1992). |
| 2624-3204 | Clockwise | bar: coding region of the phosphinothricin acetyltransferase gene from *Streptomyces hygroscopicus* Thompson et al. (1987) |
| 3205-3461 | Clockwise | 3'nos: sequence including the 3' non-translated region of the nopaline synthase gene of the T-DNA of pTiT37 (Depicker et al., 1982) |
| 3543-3743 | Counter clockwise | 3'35S: fragment of the 3' non-translated region of the 35S transcript of the cauliflower mosaic virus (Sanfaçon et al (1991) |
| 3759-6191 | Counter clockwise | synthSS2 Os mut: mutagenized coding region of the starch synthase II-3 from *Oryza sativa* (Jiang et al., 2004 or Acc. AF419099); version with a nucleotide exchange at position 2209 (adenine replaced by a guanine) prepared synthetically by DNA synthesis; DNA sequence of synthSS2 Os mut see SEQ ID No.3* |
| 6302-6821 | Counter clockwise | intron1 ubi1 Zm: first intron of the ubiquitin-1 gene (ubi1) from *Zea mays* (Christensen et al., 1992). |
| 6844-7561 | Counter clockwise | Phmw4 Ta: promoter region of the high molecular weight subunit of the glutenin 1D gene from *Triticum aestivum* (Jiang et al., GenBank Acc. No. DQ208971) |
| 8052-8076 | | RB: "right border repeat" of the T-DNA of *Agrobacterium tumefaciens* (Zambryski, 1988) |

*Supplementary note on synthSS2 Os mut: In contrast to the starch synthase II-3 from *Oryza sativa*, inter alia a restriction cleavage site for cloning EcoRV (N-terminus), a "Kozak" consensus sequence for monocotyledons pos −10 to −1 relative to the start codon (Joshi et al., 1997 PMB 35: 993-1001, "Contex sequences of translation initiation codon in plants") and a HindIII site for cloning at the C-terminus were introduced. The internal HindIII site (nt 1037-1042) was for this purpose deleted by codon switch (nt1038 A->G). Also for cloning purposes the Not I sites (nt 406-413 and 470-477) were deleted by codon switch (nt 408 G->C), (nt 470 G->C, nt 471 C->A, nt 475 C->A, nt 477 C->G). Likewise, the internal XhoI site (nt 2302-2307) was deleted by a nucleotide exchange at position 2304 (C->G).
For the purpose of optimization of the intrinsic activity of the starch synthase SS2a, a specific mutagenesis was performed on the coding region of the synthetic sequence by means of the primers Os_SS2-3-Mutag.F1 (CTg Agg gAC ACC gTg TCg gCg TTC gA = SEQ ID No. 16) and Os_SS2-3-Mutag.R1 (TCg AAC gCC gAC ACg gTg TCC CTC Ag = SEQ ID No. 17) and the Site Directed Mutagenesis Kit from Stratagene according to the manufacturers' instructions, in order to change the adenine at position 2209 of the open reading frame to guanine. As a result, a codon which codes for valine instead of methionine at the AA position 737 was created in the resulting coding region.

REFERENCES

Bolivar F., Rodriguez R. L., Greene P. J., Betlach M. C., Heyneker H. L, Boyer H. W. (1977). Construction and characterization of new cloning vehicles. II. A multipurpose cloning system, Gene, 2, 95-113.

Christensen A. H., Sharrock R. A., Quail P. H. (1992). Maize polyubiquitin genes: structure, thermal perturbation of expression and transcript splicing, and promoter activity following transfer to protoplasts by electroporation. Plant Molecular Biology, 18, 675-689.

Depicker A., Stachel S., Dhaese P., Zambryski P., Goodman H. M. (1982). Nopaline synthase: transcript mapping and DNA sequence. Journal of Molecular and Applied Genetics, 1, 561-573.

Grindley N. D. F., Joyce C. M. (1980) Genetic and DNA sequence analysis of the kanamycin resistance transposon Tn903. Proc. Natl. Acad. Sci. U.S.A. 77(12):7176-7180

Hellens R. P., Edwards E. A., Leyland N. R., Bean S, Mullineaux P. M. (2000). pGreen: a versatile and flexible binary Ti vector for *Agrobacterium*-mediated plant transformation. Plant Mol Biol 42(6): 819-832.

Jiang H., Dian W. Liu F., Wu P. (2004). Molecular cloning and expression analysis of three genes encoding starch synthase II in rice. Planta, 218, 1062-1070.

Jiang, Q.-T., Wang, X.-R., Wei, Y.-M., Zheng, Y.-L *Triticum aestivum* high molecular weight glutenin subunit 1Dx×2 gene, promoter region and 5' UTR. ACCESSION DQ208971

Sanfaçon H, Brodmann P, Hohn T. (1991) A dissection of the cauliflower mosaic virus polyadenylation signal. Genes Dev. 5(1): 141-149.

Tait R. C., Close T. J., Rodriguez R. L. Kado C. I. (1982) Isolation of the origin of replication of the IncW-group plasmid pSa. Gene. 20(1): 39-49.

Thompson C. J., Rao Mowa N., Tizard R., Crameri R., Davies J., Lauwereys M., Botterman J. (1987). Characterization of the herbicide resistance gene bar from *Streptomyces hygroscopicus*. The EMBO Journal, 6, 2519-2523.

Zambryski P. (1988). Basic processes underlying *Agrobacterium*-mediated DNA transfer to plant cells. Annual Review of Genetics, 22, 1-30.

EXAMPLE 2

Preparation and Identification of Genetically Modified Wheat Plants which Exhibit Increased SSII Activity For the production of genetically modified plants with increased starch synthase II (SSII) activity, the T-DNA of the plasmid pBA71 was transformed by the method described in Wu et al. (2003; Wu H, Sparks C, Amoah B, Jones H D (2003) Factors influencing successful *Agrobacterium*-mediated genetic transformation of wheat. Plant Cell Reports 21:659-6686) by means of agrobacteria in wheat plants of the variety Fielder and then regenerated.

The rise in the SS2 activity of the transgenic wheat plants compared to the wild type wheat plants is demonstrated in zymograms.

EXAMPLE 3

Analysis of the Starches and Flours from Genetically Modified Wheat Plants which Exhibit Increased SSII Activity The analysis of T1 grains was performed on the basis of pools from a small number of individual grains. The grain material was processed into wheat flours as described under Material and Methods and then used for the analysis of the amylose content, DSC properties, digestibility and the amylopectin side-chain distribution.

Flours from the wheat grains which contain the T-DNA for the expression of the mutagenized form of the starch synthase II-3 from rice (=synthSS2 Os mut; see SEQ ID No.3) exhibit an almost unchanged or slightly reduced amylose content compared to flours from non-genetically-modified wheat grains from wild type plants. The DSC temperatures of the flours from the transgenic wheat grains are up to 5° C. higher than those of the corresponding controls. Moreover, the flours from the transgenic wheat grains are more poorly accessible for degradation by starch-hydrolyzing enzymes, which can be discerned from a reduced content of rapidly digestible starch (RDS) and an increased content of resistant starch (RS). The structure of the starch from the transgenic wheat grains is modified insofar as it has fewer short side-chains (DP6-10) and more medium side-chains (DP11-24). This was also clearly discernible in the ratio of short side-chains to short and medium side-chains described as the ACR, which is markedly lower for the starches from the transgenic wheat plants.

a. Amylose content of flour and starch (amylose content of starch was determined by calculation, starting from a starch content by weight of 60% determined experimentally according to Method 8):

| Sample | Amylose content flour in wt. % | Amylose content starch in wt. % |
|---|---|---|
| Wild type plant variety Fielder | 17.7 | 29.5 |
| GKTA0001-2201 | 17.1 | 28.5 |
| GKTA0001-1304 | 13.8 | 23.0 |

b. DSC data of the flour (DSC analysis with 3-fold water excess)

| Sample | Tonset in ° C. | Tpeak in ° C. |
|---|---|---|
| Wild type plant variety Fielder | 62.0 | 68.2 |
| GKTA0001-2201 | 65.5 | 71.9 |
| GKTA0001-1304 | 66.9 | 73.0 |

c. RS and RDS content of the flours (=RS flour and RDS flour)

| Sample | RS flour (in wt. %) | RDS flour (in wt. %) |
|---|---|---|
| Wild type plant variety Fielder | 2.4 | 24.0 |
| GKTA0001-2201 | 15.0 | 18.6 |
| GKTA0001-1304 | 13.0 | 18.6 |

d. RS- and RDS content of the starch (=RS starch or RDS starch) (determined on a flour sample which exhibited a starch content by weight of 60 wt. % determined experimentally according to Method 8 on the flour sample. The RS starch or RDS starch value is then obtained by calculation from the RS flour or the RDS flour value by multiplying the RS flour or RDS flour value respectively by 100 and then in each case dividing by 60):

| Sample | RS starch (in wt. %) | RDS starch (in wt. %) |
|---|---|---|
| Wild type plant variety Fielder | 4.0 | 40.0 |
| GKTA0001-2201 | 25.0 | 31.0 |
| GKTA0001-1304 | 22.0 | 31.0 |

e. Side-chain distribution of the amylopectin

| Sample | DP6-11 (Sum of the areas in the chromatogram) | Ratio to wild type in % | Difference from wild type (in %) |
|---|---|---|---|
| Wild type plant variety Fielder | 21.95 | 100% | 0% |
| GKTA0001-2201 | 19.03 | 86.7% | −13.3% |
| GKTA0001-1304 | 18.59 | 84.7% | −15.3% |

| Sample | DP17-20 (Sum of the areas in the chromatogram) | Ratio to wild type in % | Difference from wild type (in %) |
|---|---|---|---|
| Wild type plant variety Fielder | 15.29 | 100% | 0% |
| GKTA0001-2201 | 16.60 | 108.6% | 8.6% |
| GKTA0001-1304 | 17.03 | 111.4% | 11.4% |

f. ACR values

| Sample | ACR value |
|---|---|
| Wild type plant variety Fielder | 0.177 |
| GKTA0001-2201 | 0.148 |
| GKTA0001-1304 | 0.143 |

EXAMPLE 4

Preparation of the Vector pBA74 for Expression of a Synthetic Form of the Starch Synthase II from Wheat (=synthSS2 Ta) in Wheat Functional Components of the Transformation Vector The vector pBA71 is a derivative of the plasmid pGREEN (Hellens et al., 2000). The "backbone" of the plasmid contains the following functional components:

[1] The "origin of replication" of the plasmid pBR322 (Bolivar et al., 1977) for replication in *Escherichia coli* (ORI ColE1)

[2] A selection marker mediating resistance to kanamycin (nptI; Grindley and Joyce, 1980) for propagation in *Escherichia coli* and *Agrobacterium tumefaciens*.

[3] The "origin of replication" of the plasmid pSA (Tait et al., 1982) for replication in *Agrobacterium* (ORI pSA)

Figure 2:
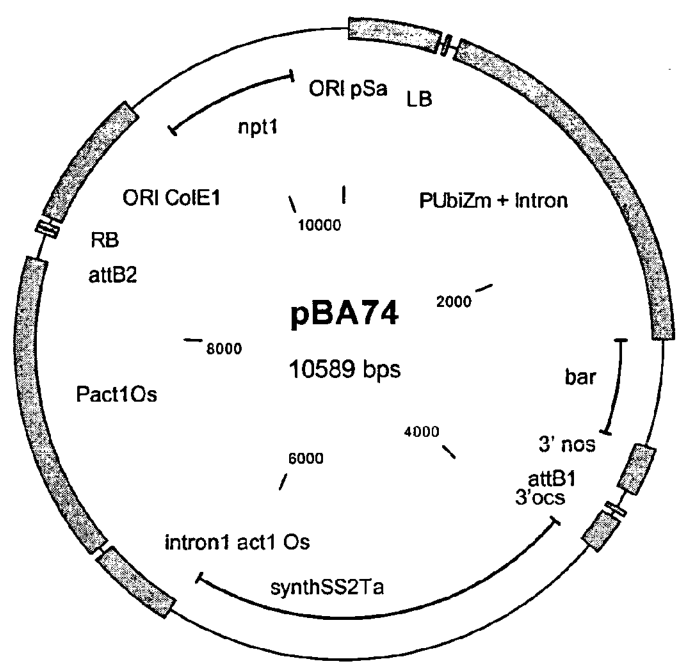
FIG. 2 shows a vector map of the pBA74 genetic components inserted into the plant genome.

The genetic components transferred into the plant genome are shown in the vector map (see FIG. 2) and described in detail in Table 2.

TABLE 2

Description of the genetic components which are inserted into the plant genome

| Nt Positions | Orientation | Origin |
|---|---|---|
| 540-563 | | LB: "left border repeat" of the T-DNA of *Agrobacterium tumefaciens* (Zambryski, 1988) |
| 615-2623 | Clockwise | PUbiZm + intron: promoter and intron of the ubiquitin-1 gene (ubi1) from *Zea mays* (Christensen et al., 1992). |
| 2624-3204 | Clockwise | bar: coding region of the phosphinothricin acetyltransferase gene from *Streptomyces hygroscopicus* Thompson et al. (1987) |
| 3205-3461 | Clockwise | 3'nos: sequence including the 3' non-translated region of the nopaline synthase gene of the T-DNA from pTiT37 (Depicker et al., 1982) |
| 3562-3587 | Clockwise | attB1: sequence including modified recognition sequence of attB from *E. coli* (Hartley et al., 2000) |
| 3543-3743 | Counter clockwise | 3'ocs: sequence containing the 3' non-translated region of the octopine synthase gene of *Agrobacterium tumefaciens* as described in De Greve et al. (1982) |
| 3828-6227 | Counter clockwise | synthSS2 Ta.: coding region of the starch synthase II from wheat as synthetic version. ** Amino acid sequence identical to the starch synthase from wheat (SEQ ID No. 6 or GenBank Acc. number CAB69544.1) |
| 6268-6729 | Counter clockwise | intron1 actl Os: first intron of the actin gene from *Oryza sativa* (rice) (Mc Elroy et al., 1990). |
| 6769-8408 | Counter clockwise | Pact1Os: sequence including the promoter region of the actin 1 gene from *Oryza sativa* (rice) (Mc Elroy et al., 1990). |
| 8549-8573 | Clockwise | attB2: sequence including modified recognition sequence of attB from *E. coli* (Hartley et al., 2000) |
| 8581-8605 | | RB: "right border repeat" of the T-DNA from *Agrobacterium tumefaciens* (Zambryski, 1988) |

** Starting from the coding region of the SS2 from wheat (see SEQ ID No. 18), to avoid cosuppression effects, the DNA sequence was synthesized in such a manner that no identical nucleotide sections with a length of more than 11 base pairs are present between the natural SS2 from wheat (SEQ ID No. 18) and the synthetic sequence (synthSS2 Ta, see SEQ ID No. 5).

REFERENCES

Bolivar F., Rodriguez R. L., Greene P. J., Betlach M. C., Heyneker H. L., Boyer H. W. (1977). Construction and characterization of new cloning vehicles. II. A multipurpose cloning system, Gene, 2, 95-113.

Christensen A. H., Sharrock R. A., Quail P. H. (1992). Maize polyubiquitin genes: structure, thermal perturbation of expression and transcript splicing, and promoter activity following transfer to protoplasts by electroporation. Plant Molecular Biology, 18, 675-689.

De Greve H., Dhaese P., Seurinck J., Lemmers M, Van Montagu M., Schell J. (1982). Nucleotides sequence and transcript map of the *Agrobacterium tumefaciens* Ti plasmid-encoded octopine synthase gene. Journal of Molecular and Applied Genetics, 1, 499-511.

Depicker A., Stachel S., Dhaese P., Zambryski P., Goodman H. M. (1982). Nopaline synthase: transcript mapping and DNA sequence. Journal of Molecular and Applied Genetics, 1, 561-573.

Grindley N. D. F., Joyce C. M. (1980) Genetic and DNA sequence analysis of the kanamycin resistance transposon Tn903. Proc. Natl. Acad. Sci. U.S.A. 77(12):7176-7180

Hartley J. L., Temple G. F., Brasch M. A. (2000) DNA cloning using in vitro site-specific recombination. Genome Research 10: 1788-1795

Hellens R. P., Edwards E. A., Leyland N. R., Bean S, Muilineaux P. M. (2000). pGreen: a versatile and flexible binary Ti vector for *Agrobacterium*-mediated plant transformation. Plant Mol Biol 42(6): 819-832.

Mc Elroy D., Zhang W., Cao J., Wu R. (1990). Isolation of an efficient actin promoter for use in rice transformation. The Plant Cell, 2, 163-171.

Tait R. C., Close T. J., Rodriguez R. L., Kado C. I. (1982) Isolation of the origin of replication of the IncW-group plasmid pSa. Gene. 20(1): 39-49.

Thompson C. J., Rao Mowa N., Tizard R., Crameri R., Davies J., Lauwereys M., Botterman J. (1987). Characterization of the herbicide resistance gene bar from *Streptomyces hygroscopicus*. The EMBO Journal, 6, 2519-2523.

Zambryski P. (1988). Basic processes underlying *Agrobacterium*-mediated DNA transfer to plant cells. Annual Review of Genetics, 22, 1-30.

The invention claimed is:

1. A wheat flour comprising a starch component having an amylose content between 15.0 wt. % and 30.0 wt. % and a content of resistant starch (RS starch) of more than 5.0 wt. %, which is obtained from a wheat plant which expresses a heterologous starch synthase II.

2. The wheat flour as claimed in claim 1, wherein the starch component has an amylose content between 18.0 wt. % and 30.0 wt. %.

3. The wheat flour as claimed in claim 1, wherein the starch component has an amylose content between 20.0 wt. % and 30.0 wt. %.

4. The wheat flour as claimed in claim 1, wherein said content of resistant starch (RS) is between 5.0 wt. % and 30.0 wt. %.

5. The wheat flour as claimed in claim 1, wherein the amino acid sequence of the heterologous starch synthase II has an identity of at least 95% with the amino acids 333 to 362 of the amino acid sequence presented under SEQ ID No. 4 and an identity of at least 95% with the amino acids 434 to 473 of the amino acid sequence represented under SEQ ID No.4 and an identity of at least 95% with the amino acids 652 to 716 of the amino acid sequence represented under SEQ ID No. 4.

6. The wheat flour as claimed in claim 1, wherein said content of resistant starch (RS) is between 16.0 wt. % and 29.0 wt. %.

7. A composition comprising the wheat flour as claimed in claim 6 and at least one food additive.

8. A foodstuff comprising the wheat flour as claimed in claim 6.

9. A foodstuff comprising a composition as claimed in claim 7.

10. The wheat flour as claimed in claim 1, wherein the starch component is granular.

11. The wheat flour as claimed in claim 10, wherein the amino acid sequence of the heterologous starch synthase II has an identity of at least 95% with the amino acids 333 to 362 of the amino acid sequence presented under SEQ ID No. 4 and an identity of at least 95% with the amino acids 434 to 473 of the amino acid sequence represented under SEQ ID No. 4 and an identity of at least 95% with the amino acids 652 to 716 of the amino acid sequence represented under SEQ ID No. 4.

12. A wheat plant cell or wheat plant which expresses a heterologous starch synthase II, wherein the heterologous starch synthase II has an amino acid sequence with an identity of at least 95% with the amino acids 333 to 362 of the amino acid sequence presented under SEQ ID No. 4 and an identity of at least 95% with the amino acids 434 to 473 of the amino acid sequence represented under SEQ ID No. 4 and an identity of at least 95% with the amino acids 652 to 716 of the amino acid sequence represented under SEQ ID No. 4.

13. A wheat plant cell or wheat plant which expresses a heterologous starch synthase II, wherein the starch synthase II is encoded by the nucleotide sequence of SEQ ID No. 3.

14. A wheat plant cell or wheat plant which expresses a heterologous starch synthase II, wherein the starch synthase II comprises the protein of SEQ ID No. 4.

15. A wheat plant cell or wheat plant which expresses a heterologous starch synthase II, wherein the starch synthase II is encoded by (a) a nucleic acid molecule which codes for a protein comprising the amino acid sequence of SEQ ID No. 4;

(b) a nucleic acid molecule comprising the nucleotide sequence of SEQ ID No. 3 or a ribonucleotide sequence corresponding hereto;

(c) a nucleic acid molecule comprising the nucleotide sequence of SEQ ID No. 5 or a ribonucleotide sequence corresponding hereto; or (d) a nucleic acid molecule, whereof the nucleotide sequence owing to the degeneracy of the genetic code deviates from the sequence of a nucleic acid molecule mentioned under (a) or (b).

* * * * *